(12) United States Patent
Dayel et al.

(10) Patent No.: US 10,018,549 B2
(45) Date of Patent: Jul. 10, 2018

(54) RAPID MEASUREMENT OF FORMED BLOOD COMPONENT SEDIMENTATION RATE FROM SMALL SAMPLE VOLUMES

(71) Applicant: Theranos, Inc., Palo Alto, CA (US)

(72) Inventors: Mark Dayel, Palo Alto, CA (US); Samartha Anekal, Palo Alto, CA (US); Elizabeth A. Holmes, Palo Alto, CA (US)

(73) Assignee: Theranos IP Company, LLC, Newark, CA (US)

( * ) Notice: Subject to any disclaimer, the term of this patent is extended or adjusted under 35 U.S.C. 154(b) by 0 days.

(21) Appl. No.: 15/132,906

(22) Filed: Apr. 19, 2016

(65) Prior Publication Data

US 2016/0341650 A1 Nov. 24, 2016

Related U.S. Application Data

(63) Continuation of application No. 13/945,147, filed on Jul. 18, 2013, now Pat. No. 9,347,867.
(Continued)

(51) Int. Cl.
*G01N 15/04* (2006.01)
*G01N 15/05* (2006.01)
(Continued)

(52) U.S. Cl.
CPC ........... *G01N 15/042* (2013.01); *G01N 15/05* (2013.01); *G01N 33/491* (2013.01);
(Continued)

(58) Field of Classification Search
CPC ............. G01N 15/05; G01N 2015/055; G01N 15/042; G01N 33/491
See application file for complete search history.

(56) References Cited

U.S. PATENT DOCUMENTS 2,982,170 A 5/1961 Wyss
3,288,019 A 11/1966 Blumenfeld
(Continued)

FOREIGN PATENT DOCUMENTS

CA 2230222 A 9/1998
CN 2259629 8/1997
(Continued)

OTHER PUBLICATIONS

Saleem et al, Comparison of Zeta Sedimentation Ratio with Westergren Sedimentation Rate, Annals of Clinical and Laboratory Science, vol. 7, No. 4, Copyright © 1977, Institute for Clinical Science.*
(Continued)

*Primary Examiner* — Daniel S Larkin
*Assistant Examiner* — David L Singer

(57) ABSTRACT

Devices and methods are described for measuring formed blood component sedimentation rate. Some of the methods may use (1) centrifugal techniques for separating red blood cells from plasma and (2) video and/or still imaging capability. Both may be used alone or in combination to accelerate formed blood component sedimentation and to measure its rate. In one example, the method may advantageously enable rapid measurement of sedimentation rate using small blood sample volumes. Automated image analysis can be used to determine both sedimentation rate and hematocrit. Automated techniques may be used to compensate for effects of hematocrit on uncorrected sedimentation rate data.

13 Claims, 24 Drawing Sheets

Related U.S. Application Data

(60) Provisional application No. 61/673,037, filed on Jul. 18, 2012.

(51) Int. Cl.
  *G01N 33/49* (2006.01)
  *G01N 15/00* (2006.01)

(52) U.S. Cl.
  CPC ............... *G01N 2015/0069* (2013.01); *G01N 2015/0073* (2013.01); *G01N 2015/045* (2013.01); *G01N 2015/055* (2013.01)

(56) References Cited

U.S. PATENT DOCUMENTS

| | | | |
|---|---|---|---|
| 3,848,796 A | 11/1974 | Bull | |
| 4,010,893 A | 3/1977 | Smith et al. | |
| 4,197,735 A | 4/1980 | Munzer et al. | |
| 4,558,947 A * | 12/1985 | Wardlaw | G01N 15/042 356/336 |
| 4,745,279 A * | 5/1988 | Karkar | G01N 21/05 250/343 |
| 4,848,900 A * | 7/1989 | Kuo | G01N 15/05 356/39 |
| 5,003,488 A | 3/1991 | Hardy | |
| 5,086,784 A | 2/1992 | Levine et al. | |
| 5,578,269 A | 11/1996 | Yaremko et al. | |
| 5,914,272 A | 6/1999 | Dufresne et al. | |
| 6,204,066 B1 | 3/2001 | Wardlaw | |
| 6,336,358 B1 | 1/2002 | Kishimori et al. | |
| 6,403,328 B1 | 6/2002 | Clampitt | |
| 6,517,475 B1 | 2/2003 | Brown et al. | |
| 9,464,981 B2 | 10/2016 | Gibbons et al. | |
| 2001/0044584 A1 | 11/2001 | Kensey | |
| 2002/0012117 A1 | 1/2002 | Wardlaw | |
| 2002/0032149 A1 | 3/2002 | Kensey | |
| 2002/0061835 A1 | 5/2002 | Kensey | |
| 2003/0078517 A1 | 4/2003 | Kensey | |
| 2003/0113930 A1 * | 6/2003 | Winkelman | G01N 15/042 436/70 |
| 2003/0205538 A1 * | 11/2003 | Dorian | A61M 1/3693 210/787 |
| 2004/0065143 A1 | 4/2004 | Husher | |
| 2008/0213743 A1 | 9/2008 | Ellsworth et al. | |
| 2011/0093249 A1 * | 4/2011 | Holmes | G06F 19/3493 703/6 |
| 2011/0226045 A1 | 9/2011 | McQuillan | |
| 2012/0015794 A1 * | 1/2012 | Holmes | A61M 1/3693 494/37 |
| 2013/0078733 A1 | 3/2013 | Holmes et al. | |
| 2013/0203107 A1 * | 8/2013 | Lalpuria | G06T 7/0012 435/34 |
| 2014/0020457 A1 | 1/2014 | Dayel et al. | |
| 2014/0315240 A1 | 10/2014 | Dayel et al. | |
| 2015/0198515 A1 | 7/2015 | Dayel | |
| 2015/0233893 A1 | 8/2015 | Dayel et al. | |

FOREIGN PATENT DOCUMENTS

| | | |
|---|---|---|
| EP | 0864854 A2 | 9/1998 |
| EP | 1063513 A2 | 12/2000 |
| EP | 1063515 B1 | 8/2006 |
| WO | 1996039618 A1 | 12/1996 |
| WO | 2008021626 A2 | 2/2008 |
| WO | 2014015177 A1 | 1/2014 |

OTHER PUBLICATIONS

Hematek, ESR Stat Plus Laser Kinetic Micro Sed Rate Analyzer, 2008.*
Lipowsky et al, Hematocrit determination in small bore tubes from optical density measurements under white illumination, Microvascular Research 20, 51-70 (1980).*
Bull, Is a Standard ESR Possible?, Laboratory Medicine • vol. 6, No. 11, Nov. 1975.*
Harper College, Measuring the Volume of Liquids, 2004.*
QBC Europe, 2008 distributer meeting technical support, 2008.*
Bull et al, The Zeta Sedimentation Ratio, Blood, vol. 40, No. 4, Oct. 1972.*
Borawski J. et al. The hematocrit-corrected erythrocyte sedimentation rate can be useful in diagnosing inflammation in hemodialysis patients. Nephron, 2001, 89(4), p. 381-383 (abstract) [online]. Retrieved from PubMed, PMID:11721153.
Notice of Allowance dated Jan. 20, 2016 for U.S. Appl. No. 13/945,147.
Notice of Allowance dated Dec. 29, 2014 for U.S. Appl. No. 14/319,644.
Office Action dated Jun. 23, 2015 for U.S. Appl. No. 13/945,147.
The international search report and the written opinion dated Dec. 19, 2013 for Application No. PCT/US2013/051143.
The international search report and the written opinion dated Jun. 4, 2015 for PCT/US2015/012537.
Office Action dated Mar. 13, 2017 for U.S. Appl. No. 14/627,307.
Office Action dated May 31, 2017 for U.S. Appl. No. 14/598,561.
Notice of Allowance dated Jan. 25, 2018 for U.S. Appl. No. 14/598,561.
Notice of Allowance dated Nov. 3, 2017 for U.S. Appl. No. 14/627,307.
Pawlotsky, et al. An Erythrocyte Sedimentation Rate Adjusted for the Hematocrit and Hemoglobin Concentration, American Journal of Clinical Pathology, vol. 122, No. 5, Nov. 1, 2004, pp. 802-810.
Schembri, et al. Centrifugation and capillarity integrated into a multiple analyte whole blood analyser, Journal of Automatic Chemistry, vol. 17, No. 3 (May-Jun. 1995), pp. 99-104.
Shelat et al. Difference in Erythrocyte Sedimentation Rates Using the Westergren Method and a Centrifugation Method, American Journal of Clinical Pathology, vol. 103, No. 1, Jul. 1, 2008, pp. 127-130.

* cited by examiner

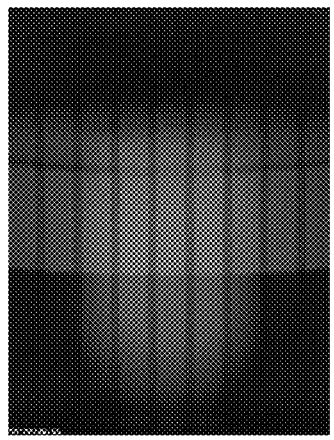 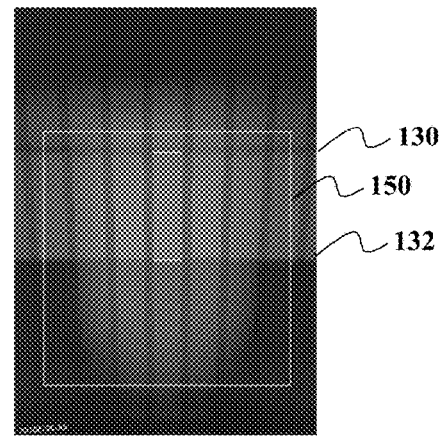
FIG. 6A  FIG. 6B
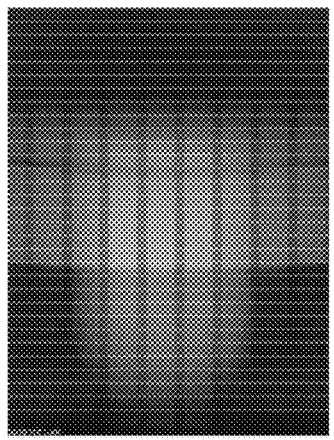 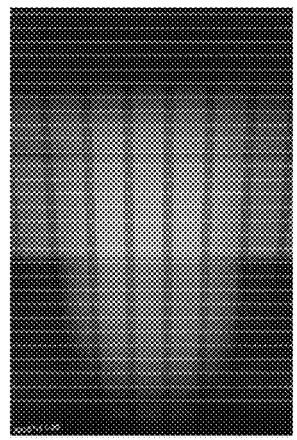 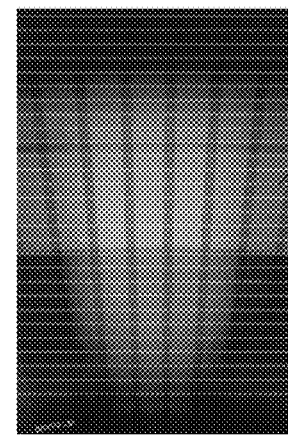
FIG. 7A  FIG. 7B  FIG. 7C

RAPID MEASUREMENT OF FORMED BLOOD COMPONENT SEDIMENTATION RATE FROM SMALL SAMPLE VOLUMES

CROSS-REFERENCE TO RELATED APPLICATION

This application claims priority to U.S. Provisional Application Ser. No. 61/673,037 entitled "Rapid Measurement of Formed Blood Component Sedimentation Rate from Small Sample Volumes" filed Jul. 18, 2012.

BACKGROUND

Erythrocyte sedimentation rate (ESR), also called a sedimentation rate or Biernacki Reaction, is the rate at which red blood cells sediment, typically measured over a period of one (1) hour. It is a common hematology test and is a non-specific measure of inflammation. To perform the test using a traditional technique, anti-coagulated blood is placed in an upright tube, known as a Westergren-Katz tube, and the rate at which the red blood cells sediment is measured and reported in mm/hour. Specifically, the Westergren method requires collecting 2 ml of venous blood into a tube containing 0.5 ml of sodium citrate. The sample should be stored no longer than 2 hours at room temperature or 6 hours at 4° C. The blood is drawn into the Westergren-Katz tube to the 200 mm mark. The tube is placed in a rack in a strictly vertical position for one hour at room temperature, at which time the distance from the lowest point of the surface meniscus to the interface between red-cell free plasma and the portion of the sample occupied by red-cells measured. The distance moved by the erythrocyte interface, expressed as millimeters in 1 hour (mm/h) is the ESR.

The ESR is governed by the balance between pro-sedimentation factors, mainly fibrinogen (but possibly also the levels of serum C-reactive protein (CRP), immunoglobulins A and G, alpha(1)-acid-glycoprotein and alpha(1)-antitrypsin), and sedimentation resisting factors, mainly the negative charge of the erythrocytes (zeta potential). In one example of the effects of inflammation, high concentrations of fibrinogen in blood plasma causes red blood cells to adhere to each other. The red blood cells adhere to form stacks called 'rouleaux,' which settle faster than individual red cells. Rouleaux formation can also occur in association with some lymphoproliferative disorders in which one or more immunoglobulins are found in high concentrations. Rouleaux formation can, however, be a normal physiological finding in horses, cats, and pigs.

ESR is increased by any cause or focus of inflammation. ESR is increased in pregnancy and rheumatoid arthritis, and decreased in polycythemia, sickle cell anemia, hereditary spherocytosis, and congestive heart failure. The basal ESR is slightly higher in females.

The standard predicate method for measuring ESR is the Westergren test, and the test uses a large volume of blood, typically several ml. It typically requires one hour incubation since many samples have ESRs as low as 10 mm/hour. Inflammatory factors which increase ESR include fibrinogen, C-Reactive Protein (CRP) and some immunoglobulins, which can increase ESR to as high as 100 mm/hour.

Traditional techniques of performing sedimentation tests have various limitations. For instance as discussed, Westergren sedimentation tests require a substantially high volume of blood to be withdrawn. Additionally, traditional sedimentation test techniques take a substantial period of time and may result in time lags in obtaining test results that could lead to delays in diagnoses and treatments which can have a deleterious effect on a patient's health.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY

It may be desirable to have sedimentation rate test that can be completed in a very short time, such as but not limited to being on the order of seconds to a few minutes. For distributed test settings, it may also be desirable to have sedimentation rate measurements that use only small blood volumes, such as can be obtained by alternate site, non-venous blood draws or minimal venous draws. It may be further desirable to make the sedimentation measurement in an automated fashion (no human observation required) and to create an objective record of the measurement. Additionally, further information useful in optimizing management of patients may be obtained by performing and/or maximizing the speed of multiplexed measurement of other analytical parameters in parallel with sedimentation rate measurement.

In one embodiment described herein, the sedimentation rate measurement method may use (1) centrifugal techniques for separating red blood cells from plasma and (2) video and/or still imaging capability. Both may be used alone or in combination to accelerate erythrocyte sedimentation and to measure its rate. Of course, techniques other than centrifugation for accelerating sedimentation may be used in place of or in combination with centrifugation to separate blood components.

In one non-limiting example, the method may advantageously enable (1) rapid measurement of ESR (seconds) with small blood sample volumes such as about 20-25 microliters ("uL" or "µL") or less, (2) use of automated image analysis to determine both red blood cell sedimentation rate and hematocrit, and/or (3) automated techniques to compensate for effects of hematocrit on uncorrected ESR so as to provide a value corresponding to the traditional Westergren method. Of course, alternative embodiments using large volumes of blood are not excluded. Because of the ability to correct for hematocrit, some embodiments of sedimentation measurement techniques described herein is more robust than traditional Westergren techniques and can be used on sample with fibrinogen and/or hematocrit levels outside the narrow range required by Westergren testing.

Using an embodiment herein, corrected ESR can be acquired in a matter of seconds using a small blood volume and which compensates for effects of hematocrit ESR. The results acquired in a matter of seconds during initial centrifugation can accelerate delivery of a diagnosis to the patient.

Moreover, in the context of multiplexed assay procedures, a common pre-processing step already involves separating red and white cells from plasma or serum prior to measurements of cellular markers and of analytes present in plasma/serum. Thus, it is convenient to incorporate an ESR measurement along with such a pre-processing procedure that will already be performed during the course of assay preparation. The ESR measurement will not create significant burden in terms of additional processing time or use of limited quantities of blood available from non-venous collection methods. By way of non-limiting example, it should be understood that assay processing, including pre-processing step(s), may occur in a single instrumented system. Optionally, some embodiments may perform one or more steps in one instrument and another one or more steps in another instrument.

It should also be understood that embodiments described herein may be adapted to have one or more of the features described below. In one non-limiting example, a typical protocol may take 20 uL of blood in a centrifuge vessel and spin in a swing-out centrifuge rotor at 4000 rpm (580*g) for about 10 s. During this time, the interface between the portion of the sample containing the red blood cells and that cleared of red blood cells is observed by video imaging. Although other time periods are not excluded, it can be advantageous to obtain the ESR measurement in this short period of time. Optionally, some embodiments may correct these "raw" ESR values for the effects of hematocrit. Hematocrit may be measured in the same operation as that used for measurement of raw ESR. In one non-limiting example, following a relatively low speed spin during centrifugation to measure ESR, the spin speed is increased to pack the red blood cells. Hematocrit is determined by image analysis of the packed red blood cells and the supernatant plasma volumes. Optionally, other techniques for measuring hematocrit may also be used to correct "raw" ESR values.

At least some of the embodiments herein may have ESR corrected without using calculations of the slope of an essentially linear transform of the non-linear (exponential) portion of the sedimentation curve.

At least some of the embodiments herein may have ESR corrected without calculating a mathematical function for a plurality of the erythrocyte/plasma interface positions occurring in a non-linear portion of the sedimentation curve.

At least some of the embodiments herein may have ESR corrected without selecting a segment of the sedimentation curve which lies in said non-linear portion of the sedimentation curve.

At least some of the embodiments herein may have ESR corrected based only on measurements of linear portion(s) of the sedimentation curve.

At least some of the embodiments herein may have ESR corrected based on measurements which consists essentially of linear portion(s) of the sedimentation curve. By "consists essentially of", we mean at least 90% or more of the measurement is based on the linear portion(s).

At least some of the embodiments herein may have ESR corrected without determining a mathematical function for a non-linear segment of the sedimentation curve representative of the magnitude of intercellular erythrocyte repulsion in the blood sample.

At least some of the embodiments herein may have ESR corrected without negating the time period during the centrifugation of the sample during which a linear portion of the sedimentation curve is formed.

At least some of the embodiments herein may have ESR corrected for hematocrit using hematocrit measurements not derived from centrifugal techniques, such as for example, lysis of red cells with detergent and mixing with ferricyanide and cyanide followed by measurement of the absorbance of the cyan-met-hemoglobin formed.

At least some of the embodiments herein may have the blood sample adjusted so that it is at a known hematocrit level for the sedimentation measurement.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

FIGS. 6A-7C show a series of corrected and uncorrected images of interfaces in a blood sample undergoing centrifugation.

DETAILED DESCRIPTION

It is to be understood that both the foregoing general description and the following detailed description are exemplary and explanatory only and are not restrictive of the invention, as claimed. It may be noted that, as used in the specification and the appended claims, the singular forms "a", "an" and "the" include plural referents unless the context clearly dictates otherwise. Thus, for example, reference to "a material" may include mixtures of materials, reference to "a compound" may include multiple compounds, and the like. References cited herein are hereby incorporated by reference in their entirety, except to the extent that they conflict with teachings explicitly set forth in this specification.

In this specification and in the claims which follow, reference will be made to a number of terms which shall be defined to have the following meanings:

"Optional" or "optionally" means that the subsequently described circumstance may or may not occur, so that the description includes instances where the circumstance occurs and instances where it does not. For example, if a device optionally contains a feature for a sample collection well, this means that the sample collection well may or may not be present, and, thus, the description includes both structures wherein a device possesses the sample collection well and structures wherein sample collection well is not present.

Figure 1:
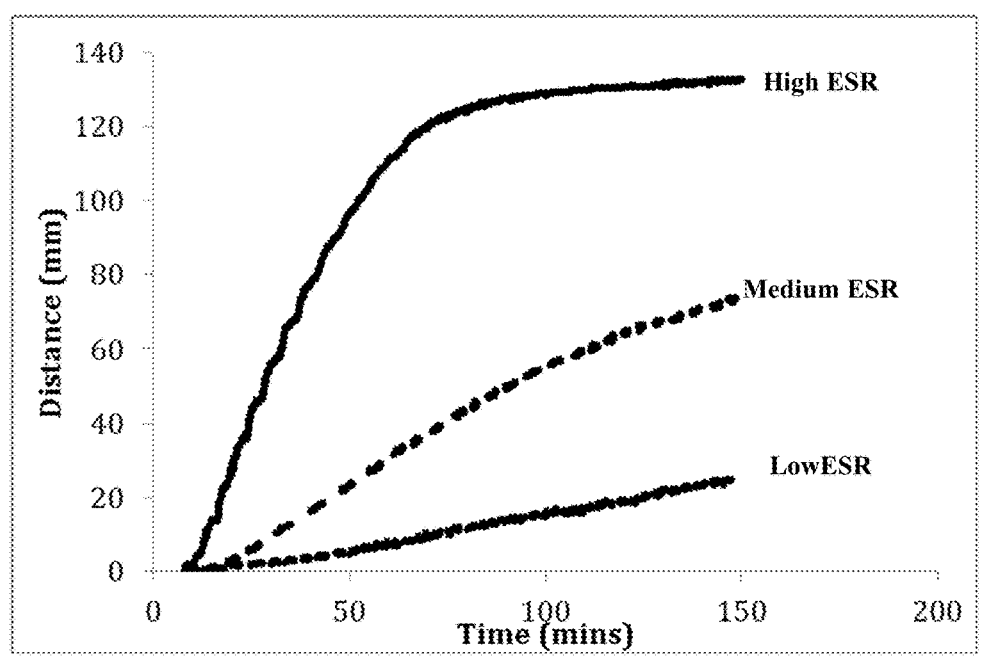
FIG. 1 shows a graph of red cell sedimentation of high, medium, and low ESR blood samples in Westergen-Katz tubes.

Referring now to FIG. 1, the kinetics of erythrocyte/plasma interface for a set of blood samples is shown. FIG. 1 shows the kinetics of erythrocyte sedimentation in Westergren-Katz tubes for a range of samples with the continuous line showing High ESR, the dashed line showing Medium ESR, and the dots showing Low ESR. Despite the reporting of the Westergren ESR as a single number (mm/hour) as seen in FIG. 1, the rate of sedimentation varies dramatically during the hour, beginning slowly, increasing, and then decreasing. The standard Westergren method records ESR at a single position at one hour, to give the mean sedimentation rate over that hour. A more recent method, called the Sigma ESR has shown better correlation with clinically relevant variables by taking the sum of the distance moved at 20, 30, 40, 50 and 60 minutes.

Sedimentation Curve Measurement

A variety of techniques may be used to establish a sedimentation rate curve for one or more formed blood components. Although the present application is described mostly in the context of measuring erythrocyte sedimentation rate, systems and methods herein can also be adapted for use in measuring sedimentation rates for other formed blood components such as but not limited to white blood cells, platelets, or the like.

In one nonlimiting example, one technique described herein comprises taking images at several time points during sedimentation by placing the sample vessel in a centrifuge, spinning for a few seconds, stopping the spin, removing the vessel, placing it in a viewer, taking an image, and repeating the above to obtain multiple images over time. From a device simplicity standpoint, it is helpful in that it simplifies hardware implementation for obtaining such images. The ability to measure sedimentation is discussed elsewhere herein where the slope from the initial (linear) part of the sedimentation curve is used to calculate the ESR.

It should be understood of course, that some embodiments may obtain such images/data regarding interface position while the container is in-situ in the centrifuge and without having to stop the centrifuge to remove the sample vessel for imaging. The in-situ images may be taken while the centrifuge rotor is in motion or at rest. It should also be understood that although discrete images may be taken, videos, continuous imaging, and multi-frame per second imaging may also be used.

Figure 2A:
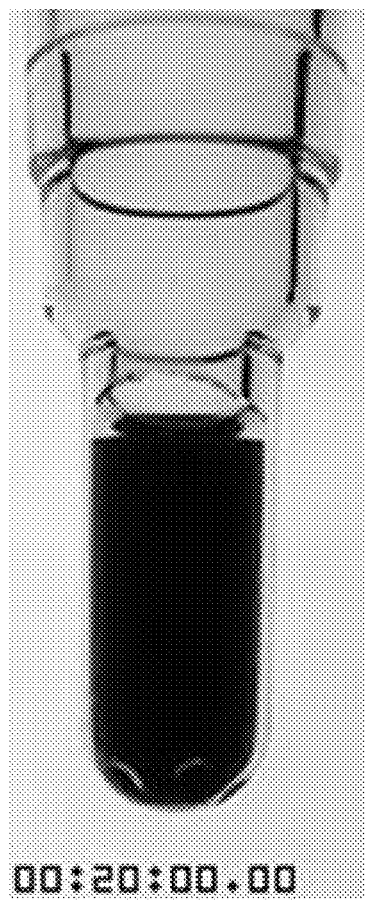
FIGS. 2A-2B are images of blood samples in transparent centrifugation vessels.
Figure 2B:
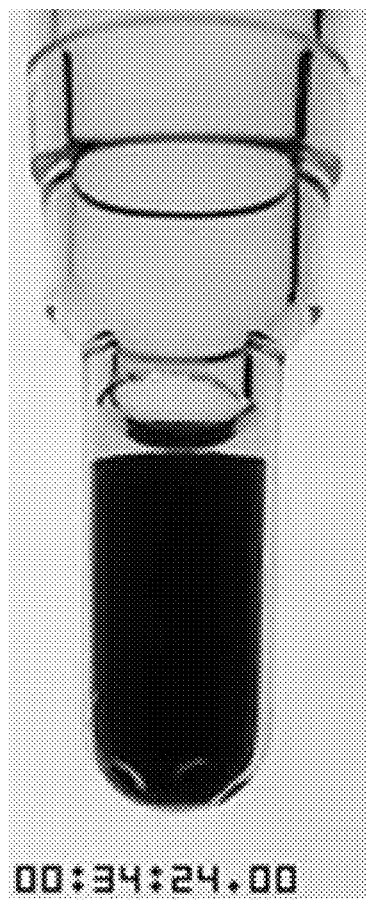

Referring now to FIGS. 2A and 2B, examples of erythrocyte interface are shown before centrifugation and at an early stage of centrifugation. By way of non-limiting example, the centrifuge vessel may be made in whole or in part of transparent material such as transparent plastic (injection-molded polystyrene). In some embodiments, the transparent portions may be windows, clear ports, or clear strips in the vessel aligned to allow for imaging of the desired blood component interface of sample in the vessel. In the present embodiment, the radius of the centrifuge vessel at its mid-point is 35 mm (radial distance from the axis of rotation). In one embodiment, outer radius is 35 mm, inner (i.e. to top surface of liquid) is 28 mm, therefore midpoint is 31.5 mm. The sample length in the vessel is 7 mm and the vessel inner diameter is 2.3 mm. Changes in the sample vessel geometry or volume of sample to be tested can be accounted for by re-calibrating the empirical parameters used for hematocrit correction factor as will be discussed elsewhere herein.

Other suitable centrifuge designs and features including dimensions for the centrifuge vessels, construction of the centrifuge rotor, and centrifuge size are disclosed in co-pending U.S. patent application Ser. Nos. 13/355,458 and 13/244,947, all fully incorporated herein by reference for all purposes. Other components of the present system including suitable imaging devices and fluid handling systems are also described in the applications incorporated by reference. For example, the ability of digital cameras such as those described in those applications may be used to measure very small distances and rates of change of distances to measure ESR. Image analysis can be used to measure the movement of the interface between red cells and plasma.

By way of nonlimiting example, in some embodiments, only two measurements taken at early times (seconds) after centrifugation has begun is sufficient to define the sedimentation rate with high precision. In one embodiment, some may take the first image after an initial minimum centrifuge speed is reached and then a second image may be taken about 10 seconds later. Of course, other time periods for the images are not excluded so long as they are in the linear portion of the sedimentation curve.

Viewing FIGS. 2A and 2B, erythrocyte interface position in a stationary (vertical) tube (short time of centrifugation) can be seen. In the present nonlimiting example, the swinging centrifugation vessel is stopped and oriented vertically in the FIGS. 2A and 2B. Of course, stationary imaging does not need tube to be vertical (so long as it is done quickly) since surface tension holds interface in place. Typically, this is done within a second or two else RBC interface will begin to flow.

As seen in FIGS. 2A and 2B, there is a clearly visible sharp transition between part of the sample occupied by red blood cells and plasma. The horizontal erythrocyte interface level is clearly visible in these images. The distance moved by the interface in FIG. 2B relative to FIG. 2A corresponds to a large number of pixels (50/mm) in the images. Thus, as seen, the number of pixels traveled by the interface allows for accurate tracking of the change in interface position. Of course, other image resolutions such as but not limited 50 pixels/mm to 1000 pixels/mm (or higher) can be used to provide even greater granularity in terms of numbers of pixels per mm or other unit length. Others may use fewer pixels per unit length so long as the resolution is sufficient to accurately determine the change in interface position. Some embodiments may magnify the image so that more pixels are associated with the interface and thus more pixels are associated with change in position of the interface. Some may use detectors with greater numbers of pixels per unit area. This increases the sensitivity of the measurement by measuring more pixels and having the ability to detect even more subtle changes in interface position.

In one embodiment, a method is provided which uses a transparent window in the centrifuge housing so that a video record of sedimentation can be made during the low-speed centrifugation. Moreover, the centrifugal field causes the meniscus to become straighter (at right angles to the centrifugal force vector) making measurement of small settling distances easier. This may be particularly true when images are captured while the centrifuge rotor is spinning. By spinning a small volume (20-25 uL) of blood at intermediate speeds (typically 4000 rpm, although 2000 to 6000 rpm may also be suitable), almost complete sedimentation of red blood cells is achieved in this embodiment within about three minutes. In practice, one method may take sedimentation measurements for a few seconds at relatively low speed (4000 rpm) then the speed would be increased to about 10,000 rpm for about three minutes to pack the red blood cells and determine the hematocrit. This multi-stage spinning at different centrifugation speeds allows for imaging for sedimentation and then rapid spin down to achieve compaction of blood components and separation from blood plasma.

Figure 3:
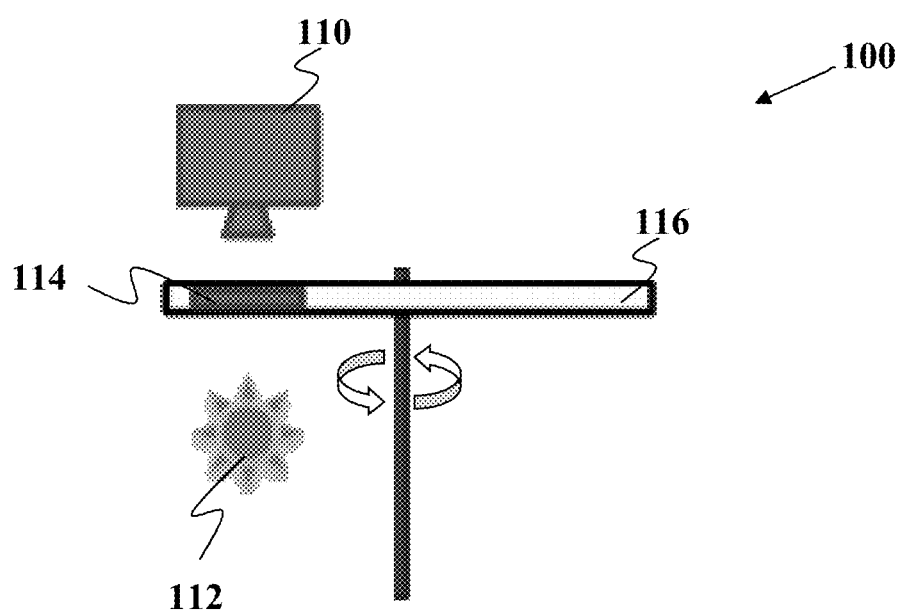
FIG. 3 shows a schematic of a centrifuge with one embodiment of a detection system.

Referring now to FIG. 3, one embodiment of a centrifuge 100 capable of monitoring interface position will now be described. To monitor sedimentation, an image capture device 110 may located near the centrifuge 100, with a light source 112 such as but not limited to a green, LED positioned to provide illumination from an opposing location. The image capture device 110 may be a still camera, a high speed camera, a video camera, or other device sufficient to detect the location of the interface. Of course, other detectors such as but not limited to non-image capture devices are also not excluded. By way of non-limiting example, one non-visual imaging device here may be a photodiode which can function as a detector to detect when a blood component interface passes the detector, or by bulk transmission of light to detect proportion of volume blocked by RBCs or other blood component(s). Non-visual imaging detectors can be used even if they may not actually convey a visual image but can still detect interface level position and/or position change in the sample.

Any descriptions of cameras, or other detection devices described elsewhere herein may apply. In one example, the image capture device 110 may be a digital camera. Image capture devices may also include charge coupled devices (CCDs) or photomultipliers and phototubes, or photodetector or other detection device such as a scanning microscope, whether back-lit or forward-lit. In some instances, cameras may use CCDs, CMOS, may be lensless (computational) cameras (e.g., Frankencamera), open-source cameras, or may use any other visual detection technology known or later developed in the art. Cameras may include one or more feature that may focus the camera during use, or may capture images that can be later focused. In some embodiments, imaging devices may employ 2-d imaging, 3-d imaging, and/or 4-d imaging (incorporating changes over time). Imaging devices may capture static images. The static images may be captured at one or more points in time. The imaging devices may also capture video and/or dynamic images. The video images may be captured continuously over one or more periods of time. Any other description of imaging devices and/or detection units may also be applied, preferably so long as they are able to detect changes in interface position.

In one non-limiting example, a light source 112 may be a light-emitting diode (LED) (e.g., gallium arsenide (GaAs) LED, aluminum gallium arsenide (AlGaAs) LED, gallium arsenide phosphide (GaAsP) LED, aluminum gallium indium phosphide (AlGaInP) LED, gallium(III) phosphide (GaP) LED, indium gallium nitride (InGaN)/gallium(III) nitride (GaN) LED, or aluminum gallium phosphide (AlGaP) LED). In another example, a light source can be a laser, for example a vertical cavity surface emitting laser (VCSEL) or other suitable light emitter such as an indium-gallium-aluminum-phosphide (InGaAlP) laser, a gallium-arsenic phosphide/gallium phosphide (GaAsP/GaP) laser, or a gallium-aluminum-arsenide/gallium-aluminum-arsenide (GaAlAs/GaAs) laser. Other examples of light sources may include but are not limited to electron stimulated light sources (e.g., cathodoluminescence, electron stimulated luminescence (ESL light bulbs), cathode ray tube (CRT monitor), Nixie tube), incandescent light sources (e.g., carbon button lamp, conventional incandescent light bulbs, halogen lamps, Globar, Nernst lamp), electroluminescent (EL) light sources (e.g., light-emitting diodes—organic light-emitting diodes, polymer light-emitting diodes, solid-state lighting, LED lamp, electroluminescent sheets electroluminescent wires), gas discharge light sources (e.g., fluorescent lamps, inductive lighting, hollow cathode lamp, neon and argon lamps, plasma lamps, xenon flash lamps), or high-intensity discharge light sources (e.g., carbon arc lamps, ceramic discharge metal halide lamps, hydrargyrum medium-arc iodide lamps, mercury-vapor lamps, metal halide lamps, sodium vapor lamps, xenon arc lamps). Alternatively, a light source may be a bioluminescent, chemiluminescent, phosphorescent, or fluorescent light source.

As seen in FIG. 3, a centrifuge vessel 114 containing a blood sample therein may be positioned so as to be between the image capture device 110 and the light source 112 to enable the position of the formed blood component interface(s) in the vessel to be visualized. The centrifuge rotor 116 may be configured to have an opening, a window, or other area that allows the centrifuge vessel 114 to be visualized during centrifugation. Measuring sedimentation during centrifugation spin may be used, but it should be understood that measuring sedimentation between spins or after spins when the centrifuge is at rest is also not excluded.

In the present embodiment of FIG. 3, the axis of rotation of the centrifuge rotor 116 may be vertical. It should be understood that other axis of rotation such as horizontal or angled axis of rotation are not excluded. Some embodiments may have a first orientation during one time period and a different orientation during a second or other time period.

Figure 4:
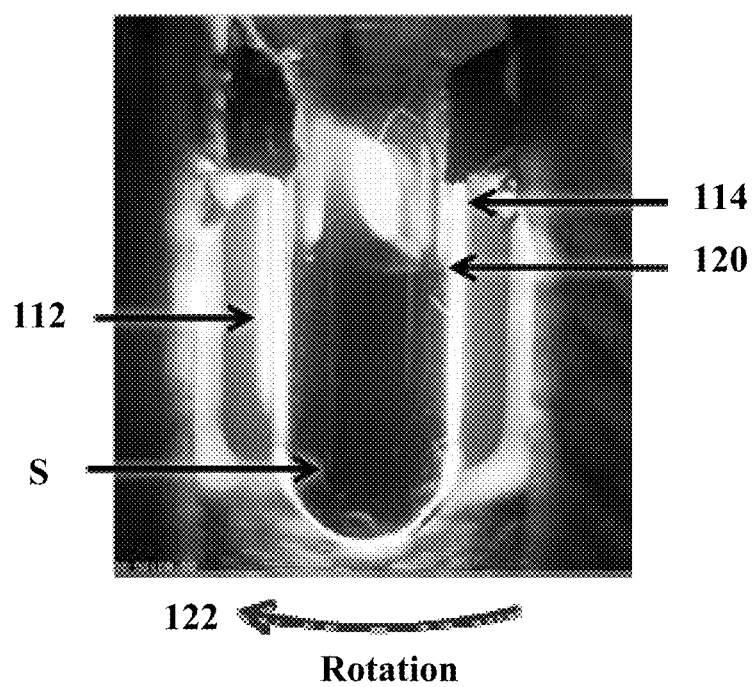
FIGS. 4-5 show images captured using one embodiment of a detection system.

In one nonlimiting example, the positions of the top and/or bottom of the centrifuge vessel are obtained by imaging as reference points, and later these are used to calibrate the liquid and interface levels. FIG. 4 shows a camera view of a centrifuge vessel 114 in the centrifuge. Illumination from light source 112 from behind the centrifuge vessel 114 allows for visualization of blood sample S and the blood/air interface 120. The direction of rotation is shown by arrow 122.

Figure 5:
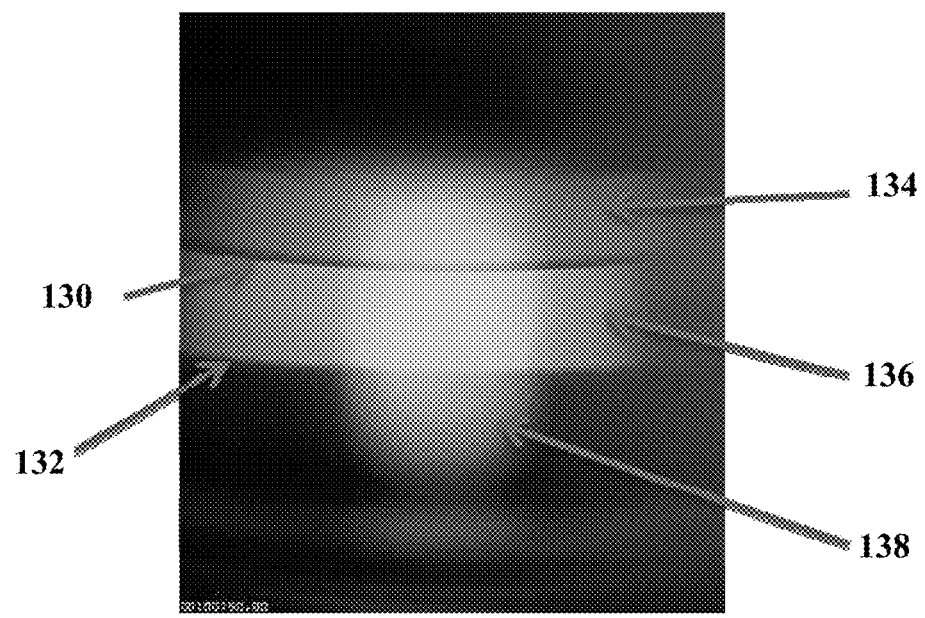

Referring now to FIG. 5, an enlarged view of the interface(s) of the blood sample in the centrifuge vessel 114 will now be described. FIG. 5 is an image of sedimenting red blood cells during centrifugation. Air/plasma interface 130 and plasma/red blood cell interface 132 are clearly discernable as sharp lines (separating spatial regions of different contrast) in the image. Space 134 above the air/plasma interface, plasma 136, and light 138 blocked red blood cells are also shown in the image of FIG. 5.

It should be understood that strobe illumination or capture frames synchronized to the rotor position are not excluded, but in the present embodiment, are not required for image capture. In this nonlimiting example for the image of FIG. 5, a 200 ms exposure (short relative to spin times) for the CCD camera image acquisition makes the interfaces 130 and 132 clearly visible during the spin (see FIG. 5). This was long compared to the rotation period (i.e. that many rotations occur during the time, so that images blur out). The image blurs around the rotor axis so that the air/plasma interface and plasma/erythrocyte interface are visible as arcs (though there are maybe strobe effects that may also be taken into account). Although the data acquisition does not require frame capture to be synchronized to rotation, some embodiment may use synchronization. Optionally, some embodiments without synchronization may cause striping, which can be compensated for by a combination of longer exposures and image processing. Other embodiments may use faster image acquisition techniques to generate images that minimize and/or eliminate blurring. Some embodiments may use strobe illumination or other techniques to capture images of fast moving objects such as the sample containing vessel during centrifugation.

As seen in FIG. 5, light transmitted through two regions of the centrifuge vessel 114 may include the air 134 above the liquid, and the plasma between the air/plasma and plasma/erythrocyte interfaces 130 and 132 as labeled. The air/plasma interface 130 itself is visible as an arc. Essentially no light makes it through the vessel 114 where the erythrocytes are (although it should be understood that this region is not completely dark because of the light transmitted when the vessel 114 rotates out of the blocking position).

In one embodiment, images are captured for three minutes at five frames per second, with long exposure (~200 ms), then processed to extract the sedimentation curve. Optionally, the rate of imaging includes but is not limited to 1, 2, 4, 8, 16, 32, 64, or 128 images per second. Optionally, exposure time includes but is not limited to 10, 20, 40, 80, 160, 320, or 640 ms. Temperature during measurement may also be varied. Although many embodiments herein had measurements performed at room temperature, but other temperatures e.g. 37° C. are not excluded. Effect of temperature would be taken into account in the calibration, such as for determining empirical parameters of the correction factor. Also, time to centrifuge spin up was typically about 3 seconds, but faster or slower spin up times are not excluded.

By way of nonlimiting example, the sedimentation rate of the desired formed blood component being measured may be defined by:
1) fitting the plasma/red blood cell interface position versus time to an exponential, or
2) taking the (linear) rate of interface movement over the first few seconds to give a parameter, which can then be correlated with Westergren ESR.

Although others settings are not excluded, it should be understood that times of sedimentation are usually defined as starting following the rotor 116 reaching its target speed when the buckets holding the centrifuge vessels 114 are oriented radially in the spin plane and so are in optimal position for image capture and processing.

Data Pre-Processing
Image Transformation

Referring now to FIGS. 6A-6B, one embodiment herein may use an image pre-processing step prior to analysis which may be a combination of (1) conversion of the interface arc to a flat interface and (2) rotation of the image to compensate for any minor offsets in the radial direction. This brings off-center pixels in line with the central axis in a way that has negligible effect on the y positions of the interfaces so that the blurred-out arcs from the rotating tube are now horizontal stripes.

As seen in in FIGS. 6A-6B, an initial image transform may be used to compensate for arcs. The image in FIG. 6B shows a rectangle 150 with the selected area of interest across which the horizontal averaging is performed, and two short horizontal lines showing where the algorithm has identified the position of the air/plasma interface 130 and the plasma/erythrocyte interface 132.

This image transformation is desirable to remove the effects of the vertical lines seen in FIG. 6A, caused by a strobe effect between the frequency of rotation of the centrifuge and the acquisition frequency of the camera. A thin vertical (i.e. radial) section measurement would be vulnerable to these lines, which move slowly across the image, but the straightening transform allows averaging in the x-direction (at right angles to the radial) and makes the profile immune to the effects of the moving lines. This procedure also improves the signal to noise ratio.

Referring now to FIGS. 7A-7C, examples showing different degrees of arc compensation are shown. Selection of image transformation parameters can be chosen to introduce a desired level of correction. FIG. 7A shows compensation that is too little. FIG. 7B shows compensation that is just right. FIG. 7C shows too much arc compensation.

For each dataset using a script that produces a series of images with different arc and rotation angle correction, superimposing a series of horizontal lines 160 on the images allows for judgment of when the interfaces are flat (horizontal in the images of FIGS. 7A-7C). This judgment of appropriate degree of arc correction can be determined by a programmable processor configure for image processing, pre-set based on a calibration procedure, or may be selected based on human review.

Once these parameters are selected, the acquired image information, which may be a video, is put through the transformation. A region of interest may be chosen that covers both the whole range of positions for both the air/plasma interface 130 and the erythrocyte interface 132. Optionally, some embodiments may choose a region of interest covering only one of the interfaces 130 or 132. Optionally, some embodiments may be configured to target one or more other areas of interest in the sample.

Sedimentation Curve Extraction

Figure 8A:
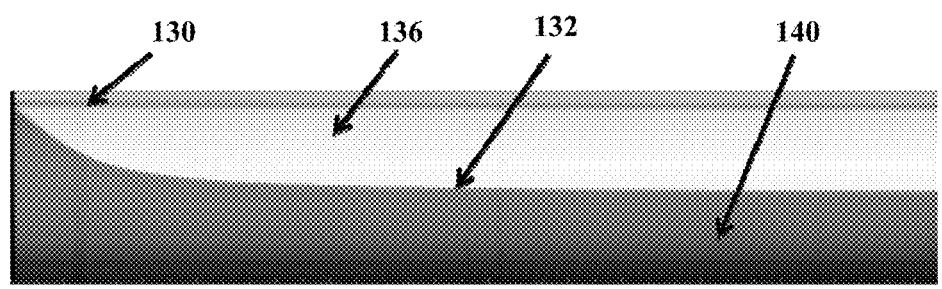
FIGS. 8A-8B show various kymographs for one test sample.
Figure 8B:
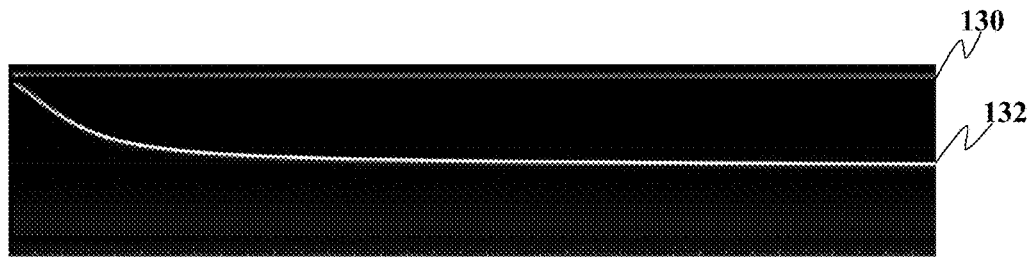

Referring now to FIGS. 8A-8B, for each timepoint in the plurality of images, one embodiment of the technique herein averages the pixel intensity values for each row (across the vessel 114) within the region of interest 150 to produce a single column representing the intensity radially down the vessel. The columns for each timepoint are then assembled into a kymograph, i.e. an image where the x-axis represents time and the y axis represents radial position along the tube.

FIG. 8A shows a kymograph according to one embodiment described herein. The kymograph of FIG. 8A shows average image intensity down the tube (y-axis) over time (x-axis). FIG. 8A shows an air interface 130, plasma 136, plasma/red blood cell interface 132, and red blood cells 140. More specifically, the dark horizontal line near the top of the image represents the air/plasma interface 130, the bright area below it represents the light transmitted through the plasma 136, and the dark area at the bottom is where the light is blocked by the red blood cells 140.

FIG. 8B shows that, to extract the position of the air/plasma interface and the plasma/erythrocyte interface, a first derivative (edge detection) of the interface with respect to time may be determined. Derivative is with respect to distance down the tube (y-axis) and not time (x-axis). FIG. 8B shows the positions of the air/plasma (upper) interface 130 and plasma/erythrocyte (lower) interface 132.

In one nonlimiting example, the positions of the two local maxima of the image in FIG. 8B, one representing the air/plasma interface and other the plasma/erythrocyte interface are determined. To convert these (pixel) positions into volume occupied by the whole sample and volume occupied by red blood cells, the y-position of the top and bottom of the centrifuge tube (such as recorded from the stationary tube image shown in FIG. 2) are used as reference locations together with knowledge of the shape of the centrifuge vessel.

Figure 9:
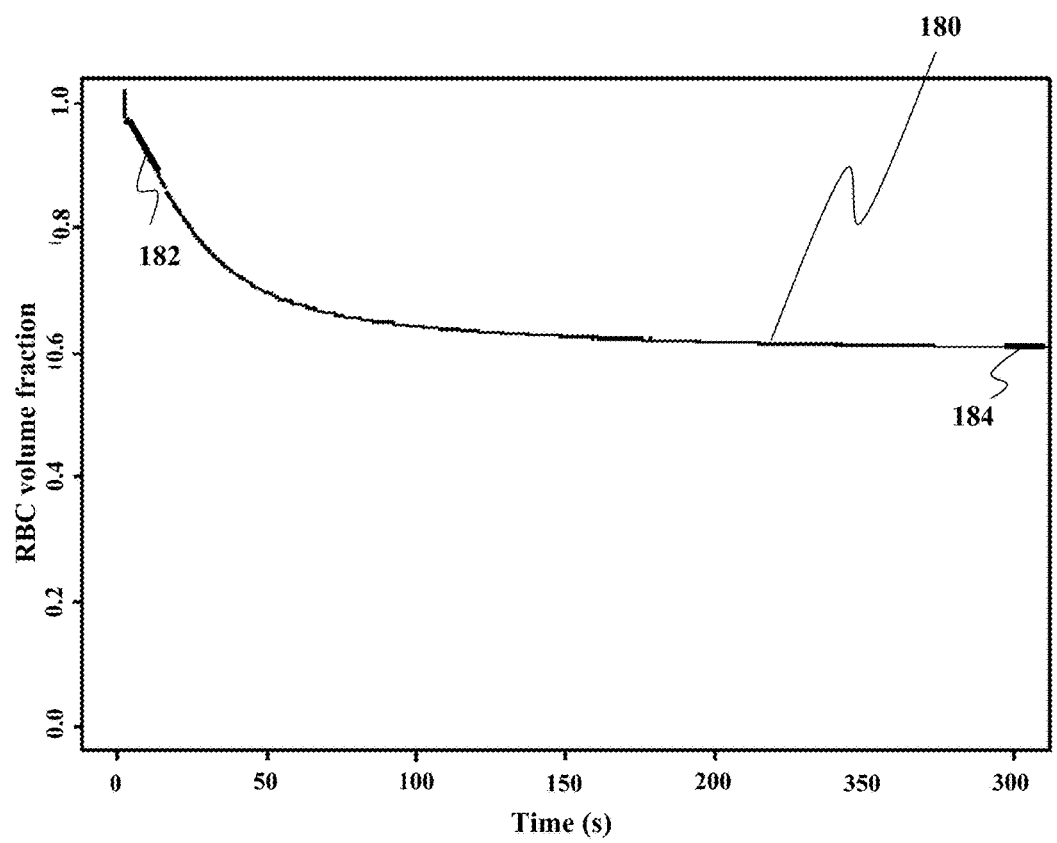
FIG. 9 shows a sedimentation graph for one test sample

As seen in FIG. 9, the plasma/erythrocyte interface position is converted to the volume fraction occupied by red blood cells and plotted against time as a centrifuge-assisted sedimentation curve 180. This curve in FIG. 9 is the result of one nonlimiting example of a centrifuge-based method of determining a sedimentation curve extracted from a video record.

Calculating ESR from Sedimentation Curve

Once the sedimentation curve of FIG. 9 is obtained for each sample, there are many possible ways to extract parameters that correlate with ESR. One simple way to reduce the curve to a single parameter for analysis is to fit a single exponential to the curve of the plasma/erythrocyte interface using standard nonlinear least squares fitting.

Figure 10A:
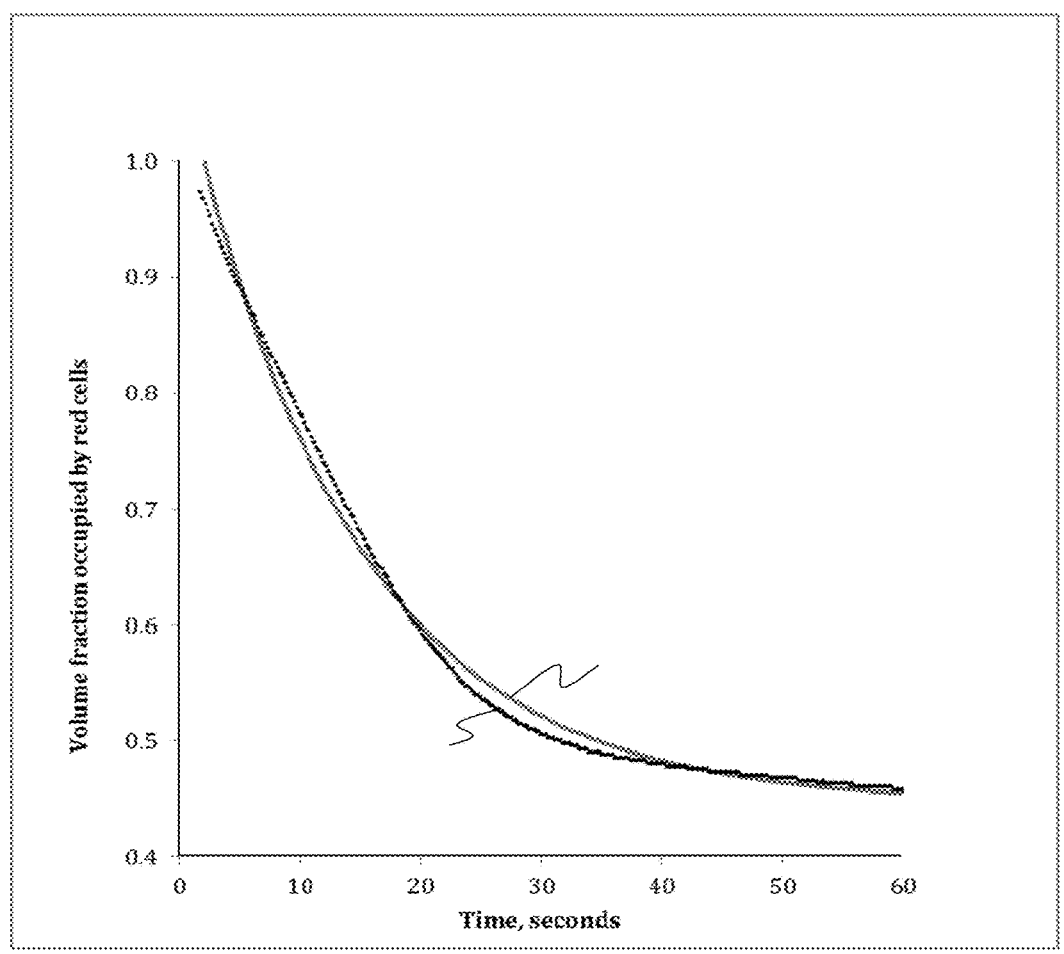
FIGS. 10A-10B show sedimentation graphs with various fitted functions fitted to the data of FIG. 9 plotted thereon.

One such example is shown in FIG. 10A. For FIG. 10A, data in the graph is shown as black dots 200, the x-axis is time in seconds, and the y-axis is the volume fraction occupied by red blood cells. A single exponential fit is shown as line 202.

Figure 10B:
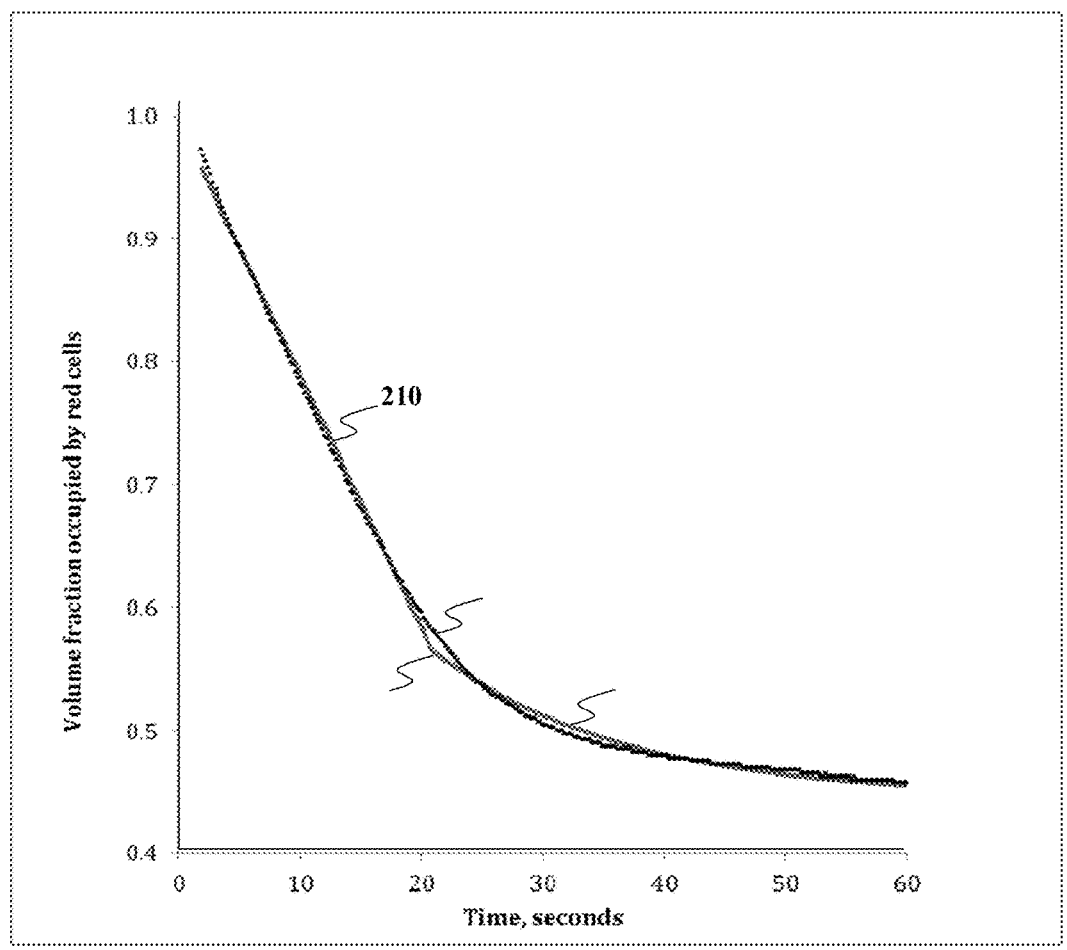

Referring now to FIG. 10B, data in the graph is shown as black dots 200. FIG. 10B shows a substantially bi-linear fit. The gradient of the initial linear portion shown by linear fit 210 may be determined, as well as the time 212 of the transition between the initial linear section, and the non-linear region where packing slows, shown here by the red line 214.

Although these simple techniques of using standard non-linear least squares fitting may yield some information related to ESR, when comparing such measurements with traditional Westergren ESR measurements, the correlation based on the nonlinear least squares (NLS) fitting leaves room for improvement as NLS by itself does not take into account certain correction factors.

Plasma Protein Impact on ESR

To extract ESR parameters that more closely correlate with traditional Westergren ESR measurements, it is helpful to understand some factors which may impact ESR measurements. The parameter of interest (ESR) responds to the concentration of certain plasma proteins and can be directly affected/manipulated by adding one of these proteins, (e.g., fibrinogen) to the blood sample.

Figure 11:
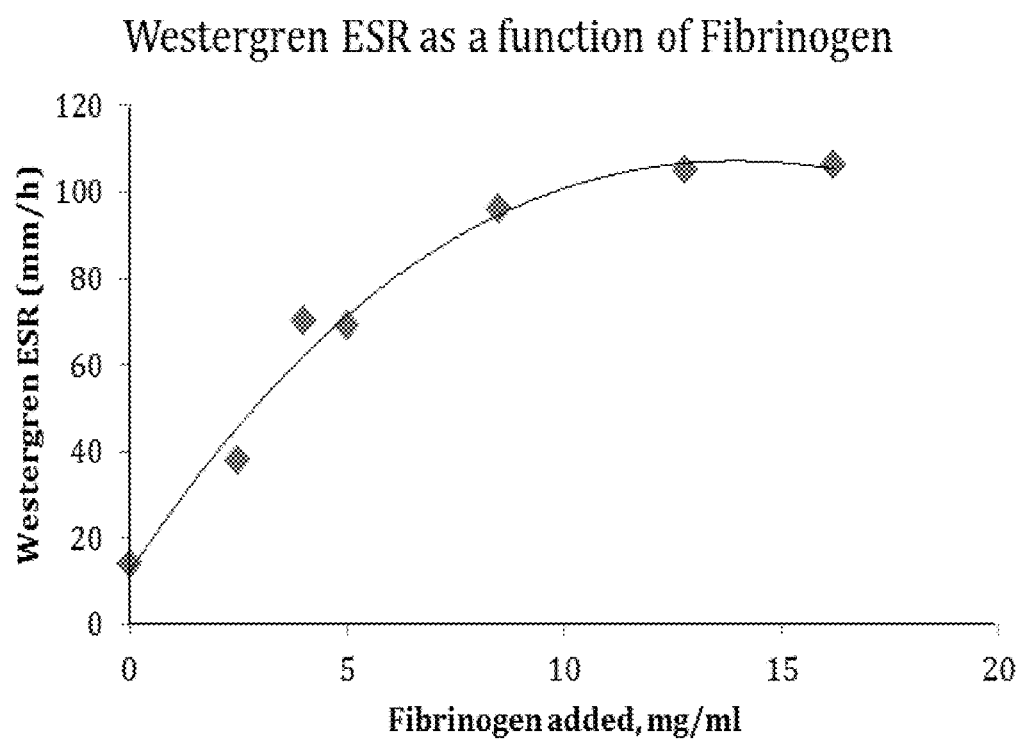
FIGS. 11-14 are graphs showing various sample sedimentation characteristics for samples with various levels of added fibrinogen.

In the present example, as a technique to provide samples with a wide range of ESR values, exogenous fibrinogen was used to create blood samples with ESR values spanning the whole range of interest (0-120 mm/h in the Westergren method). FIG. 11 shows how adding fibrinogen increases the Westergren ESR values.

Figure 12:
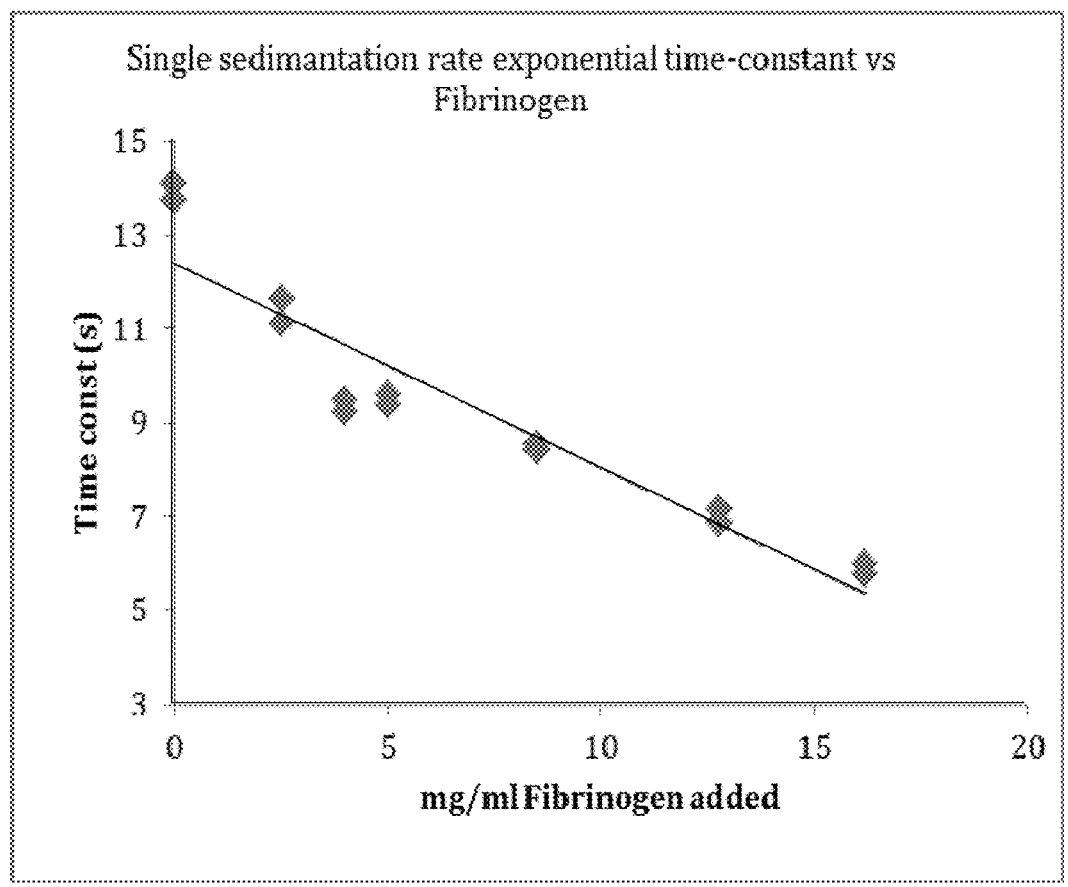
Figure 13:
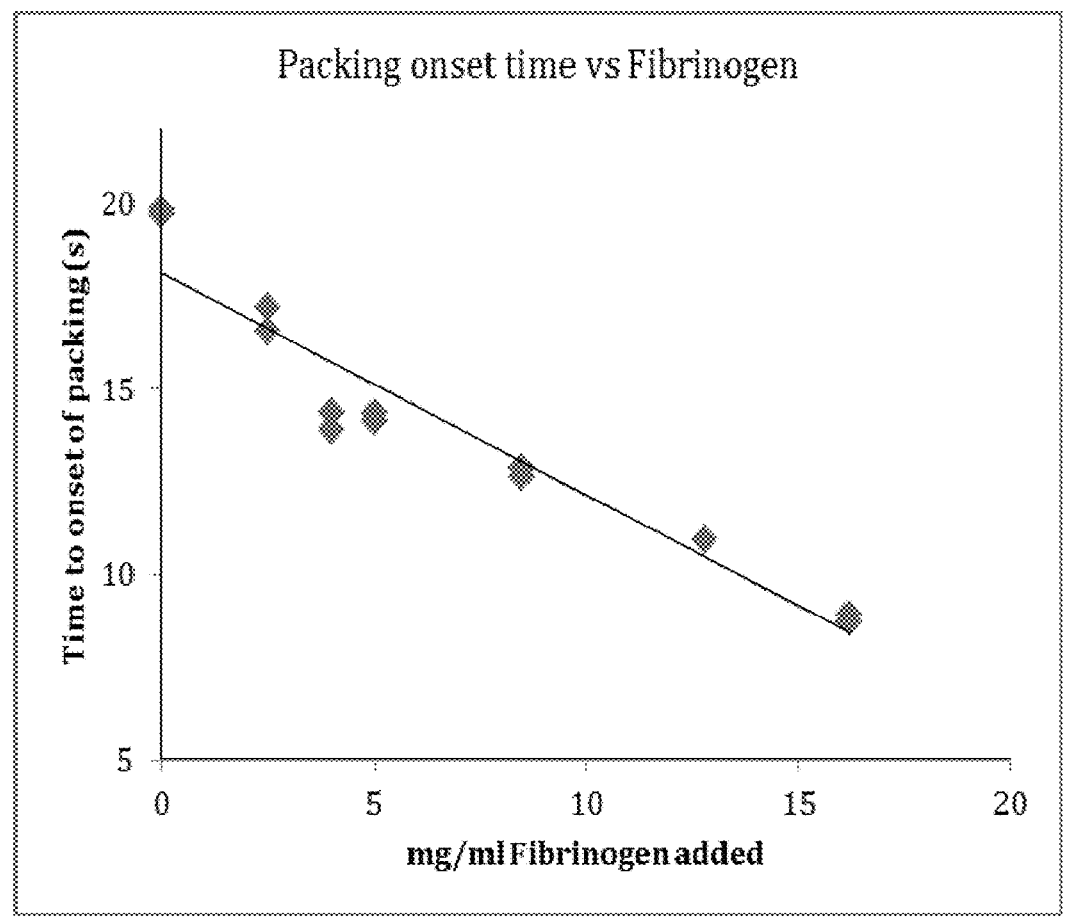
Figure 14:
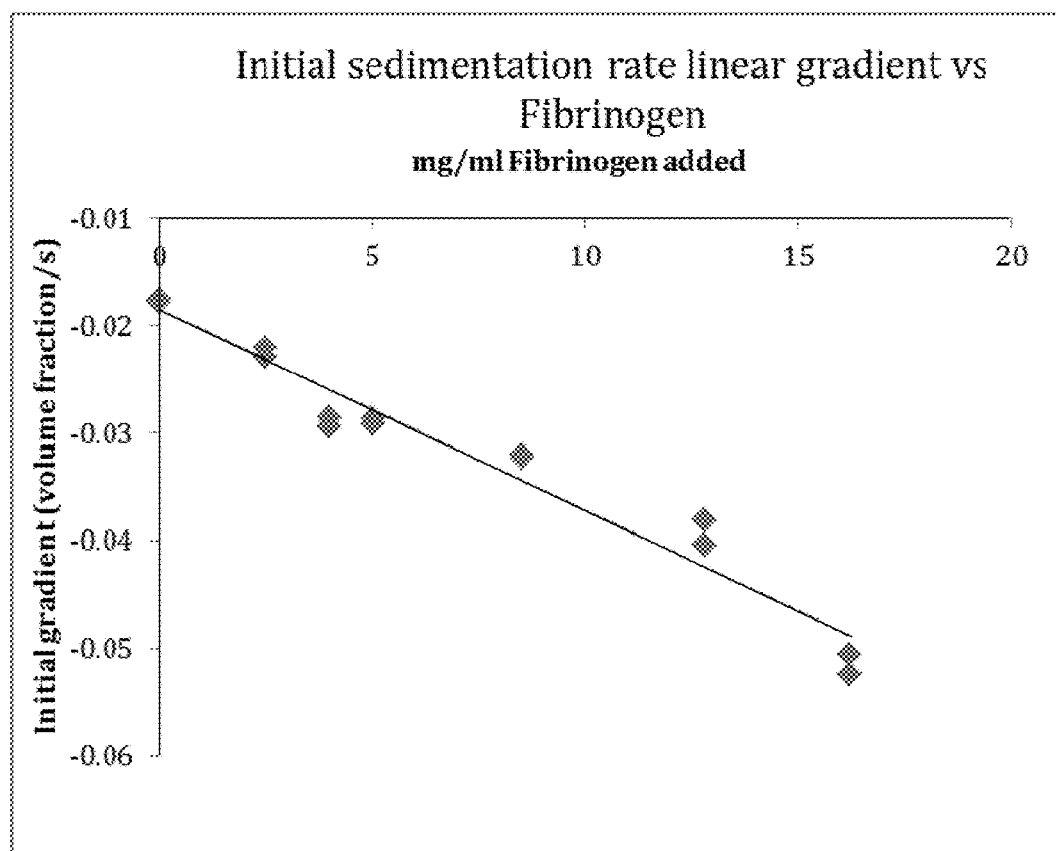

As seen in FIGS. 11 to 14, several parameters from centrifugal analysis show a good correlation with fibrinogen levels (and therefore with ESR), most notably the time constant from a single exponential fit, the time to onset of packing, and the initial linear gradient. Referring to FIGS. 12, 13, and 14, in some embodiments, each of these parameters can be used to obtain an estimate of the Westergren ESR value. The single exponential-fit time constant and the packing onset time both have the advantage of being independent of y-scale. The packing onset time and the initial linear gradient have the advantage of having clear physical meanings.

FIG. 11 shows that Westergren ESR values increase with increasing added fibrinogen. FIG. 11 illustrates a single sample with different levels of fibrinogen added therein.

FIG. 12 shows a time constant from a single exponential fit of the raw sedimentation curve which shows good correlation with added fibrinogen levels FIG. 13 shows time to the onset of cell packing which shows good correlation with added fibrinogen levels.

FIG. 14 shows initial linear gradient of the raw sedimentation curves which show good correlation with added fibrinogen levels.

Hematocrit Impact on ESR

It should be understood that, in addition to fibrinogen, hematocrit is another factor that affects Westergren and other ESR measurements. In fact, Westergren erythrocyte sedimentation is strongly affected by hematocrit. In the Westergren method, many laboratories either do not report results for samples with hematocrits greater than about 45% or adjust the sample hematocrit to a fixed level (usually 45%) before measuring ESR. The present embodiment of the method is actually better than the Westergren technique, in that Westergren saturates (i.e. does not respond to fibrinogen <10 mg/ml), whereas the present embodiment of the method does not saturate out to 15 mg/ml.

Centrifuge-based ESR sedimentation is even more strongly affected by hematocrit levels than measurements under gravity. For at least some embodiments here, the increased dependency on hematocrit is also because of the lower volumes—and consequently smaller vessel dimensions. Increasing hematocrit typically means the erythrocytes start closer together, increasing the viscosity of the blood by presenting physical barriers to free movement, and decreasing the maximum distance the interface can move before the cells become packed, all of which decrease the ESR, independent of fibrinogen from inflammation.

To illustrate the dramatic confounding effect of hematocrit, centrifuge-based ESR measurements, performed by taking the same sample of blood and adjusting the hematocrit before measuring the ESR, show that a person with a typical hematocrit of 45% and a normal ESR of 22 mm/h would register as 5 mm/h (very low) if the hematocrit were 60% and 93 mm/h (very high) if the hematocrit were 35%, even though there are no changes in the plasma protein levels which are clinically important. In other words, variations of ESR due to hematocrit can dominate variations of ESR due to plasma proteins the clinician is interested in.

There are several traditional approaches to compensating for this confounding effect of hematocrit. One approach is using the hematocrit compensation curves, e.g. from Dintenfass (1974). Rather than correcting for hematocrit using a chart, a more accurate (if more labor-intensive) way to remove the confounding effect is simply to alter the hematocrit to a standard value before the test. Some ESR techniques, e.g. the 'hematocrit corrected ESR' include an initial such step that fixes the hematocrit to a set value e.g. 45%, so that the measured ESR really reflects the protein content of the plasma (clinically relevant), rather than the hematocrit (Borawski and Myśliwiec 2001).

Figure 15:
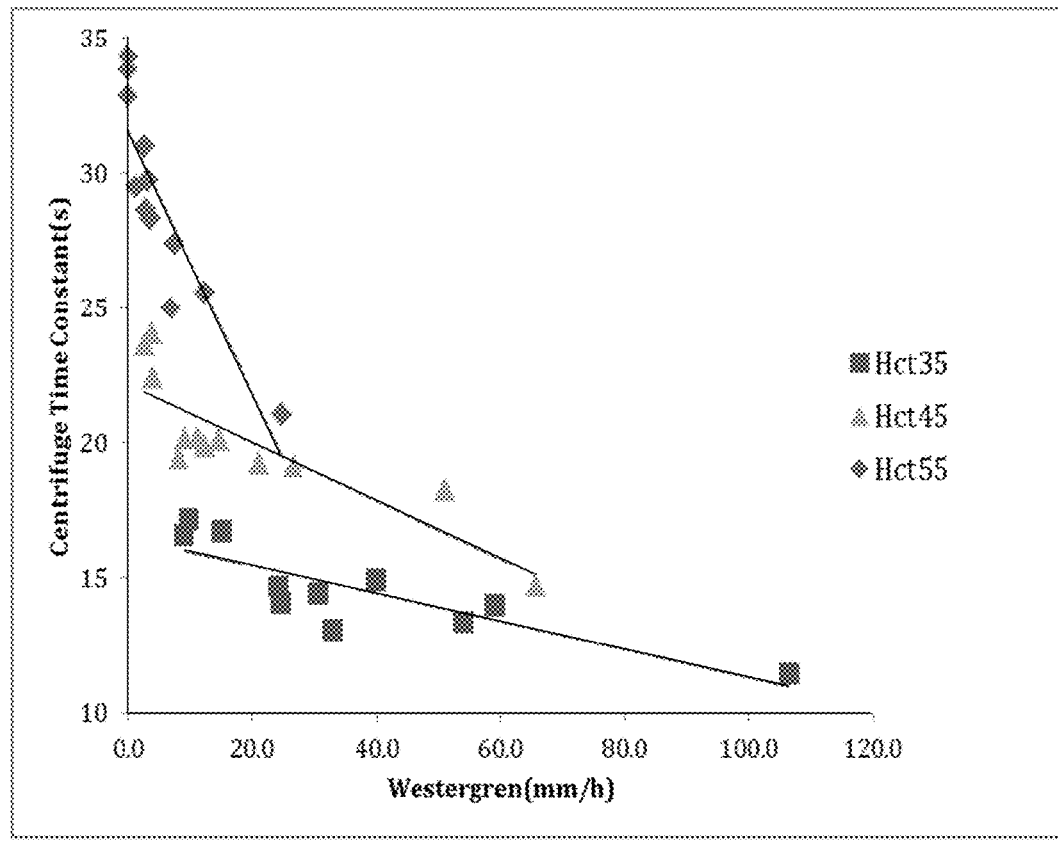
FIG. 15 shows sedimentation rates for several blood samples manipulated to have different hematocrit levels.

As seen in FIG. 15, to understand and estimate the effects of hematocrit, a set of eleven (11) samples were adjusted to 35%, 45% and 55% hematocrit, then tested by the centrifuge ESR and Westergren ESR techniques. Correlations are shown for centrifuge single exponential time constant with Westergren ESR for hematocrit adjusted clinical blood samples. Samples correlate well within each hematocrit, but samples are not well correlated across all hematocrits.

Figure 16:
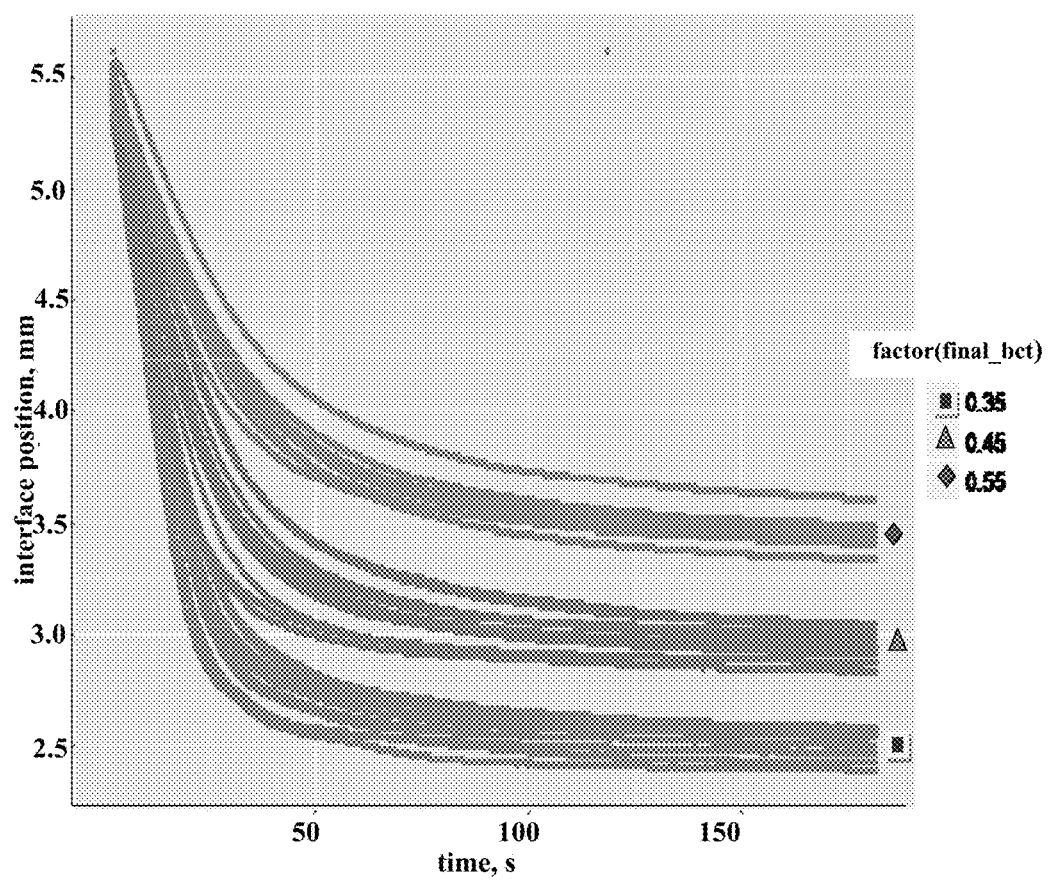
FIG. 16 is a graph of interface positions over time for the samples with different hematocrit levels also shown in FIG. 15.
Figure 17:
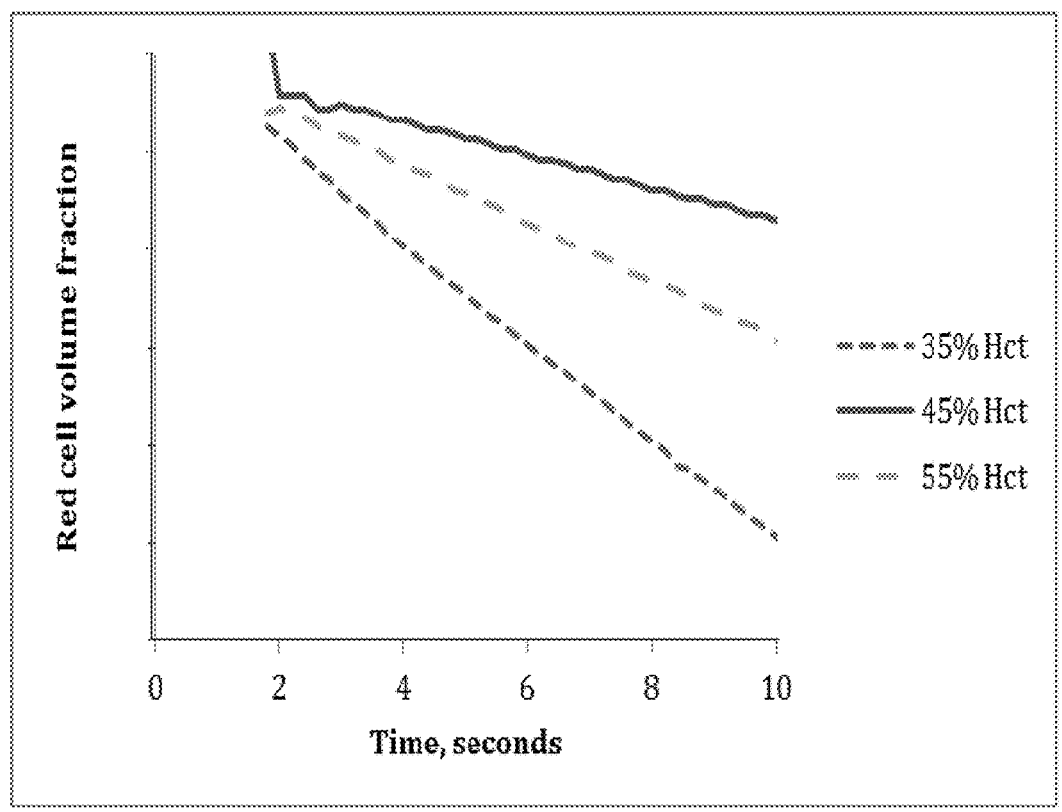
FIG. 17 is a graph of interface positions over a 10 second period of time for one sample with different hematocrit levels.

Referring now to FIG. 16, the position of plasma/erythrocyte interface as a function of time is plotted on the chart for different clinical samples with different hematocrit levels for centrifuge-based ESR experiments. Several blood samples having unadjusted and adjusted fibrinogen levels and hematocrits are shown: red square: 35%, green triangle, 45% and blue diamond 55% hematocrit. FIG. 16 shows complete sedimentation profiles while FIG. 17 shows sedimentation profiles for a shorter period of time (<10 s) for an initial measurement period for one sample adjusted to the given hematocrits. The sedimentation profiles for the samples show a sharp descent during the initial measurement period, with the interface position falling almost linearly with time during that initial measurement period. The sedimentation rate then slows as the red blood cells pack together. Many data sets corresponding to various hematocrits (as indicated) and various ESR rates are shown in FIG. 16.

In FIG. 17 where sedimentation over short initial time periods (<10 s) are shown, the high quality of the data obtained with such short measurement times show a linear sedimentation rate for all hematocrit levels during the initial period. In one embodiment described herein, the linear region of the sedimentation profiles can be used to extract a sedimentation velocity. The raw sedimentation velocities are plotted against Westergren ESR. Given that the three fit lines corresponding to the three hematocrit levels in FIG. 17 are discontinuous, compensation for hematocrit is desirable to derive the clinically significant ESR value from the raw value.

Figure 18A:
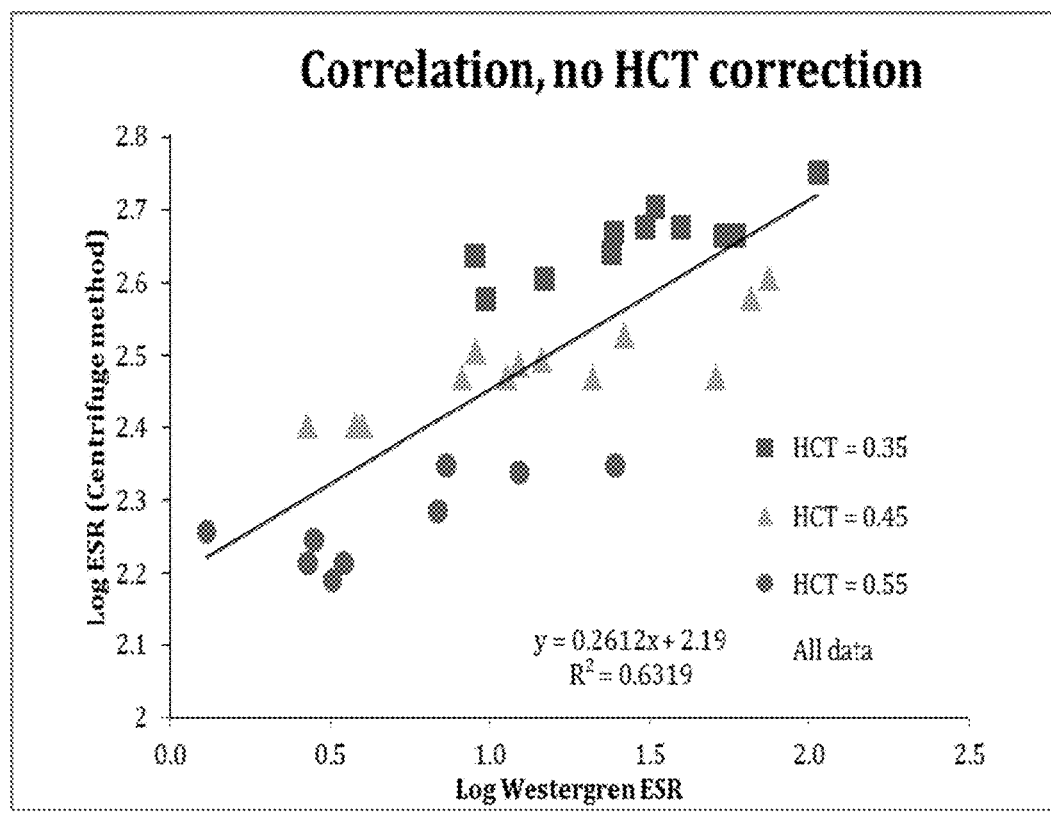
FIG. 18A shows an ESR graph of one embodiment herein without hematocrit correction.

As a further example, FIG. 18A shows the logarithm of the erythrocyte sedimentation rates extracted from sedimentation profiles uncorrected for hematocrit). FIG. 18A also shows that centrifuge-based sedimentation rates are strongly dependent on hematocrit, more so than the Westergren-based sedimentation rates. The narrow cross-section of the centrifuge tube increases hydrodynamic resistance to fluid flow due to red blood cells. The centrifugation process involves flow of plasma through a bed of red blood cells, which offer hydrodynamic resistance. This resistance is a function of the volume fraction of red blood cells, i.e., the hematocrit.

To obtain a better correlation between the centrifuge-based and Westergren sedimentation rates, the centrifuge-based sedimentation rates were corrected for effect of hematocrit. The correction used can be represented by, $$U_{corr} = \frac{U_{uncorr}}{\left(1 - \frac{\varphi}{\varphi_{max}}\right)^{\gamma}},$$

where $U_{uncorr}$ and $U_{corr}$ are the uncorrected (raw) and corrected sedimentation rates respectively, $\varphi$ is the volume fraction of cells (hematocrit), and $\varphi_{max}$ and $\gamma$ are empirical parameters obtained by curve fitting. The correction factor represents a simple mathematical form to account for the increased drag exerted by red blood cells. It should be understood that this functional form was found to be able to correct for hematocrit, but other functions would work too.

By way of non-limiting example, one way of calculating $\varphi_{max}$ and $\gamma$ is by way of a calibration technique such as but not limited to the following: for a diverse set of samples (different hematocrits, ESR values, etc. . . . ), the ESR value is determined using a reference method, and by the centrifuge-based method. The $\varphi_{max}$ and $\gamma$ parameters are determined as a calibration for each centrifuge setup and may change based at least in part on vessel geometry and volume of sample. Thus, if at least one of those factors is changed, it may be desirable to re-calculate the parameters. For one centrifuge setup as described herein, optimal values of these parameters were obtained as: $\varphi_{max}=1.67$ and $\gamma=3.85$. It should be understood that these parameters are for fit optimization and do not relate directly to physical parameters.

Hematocrit Measurement Techniques

For purposes of calculating the hematocrit correction factor, it should be understood that the value for hematocrit may be known prior to the start of the centrifuge-based sedimentation test and in such situations, corrected ESR results can be obtained quickly based on the initial linear portion of the sedimentation and the known hematocrit level, without having to wait until the erythrocytes have been fully compacted by centrifugation. Optionally, some embodiments may determine hematocrit levels during or after centrifugation.

Hematocrit measurement by non-centrifugal before, during, or after centrifugation includes at least the following. One technique involves measurement of hemoglobin concentration. For example, in roughly 99% of the population, there is a 1:1 correlation between hemoglobin measurements and hematocrit levels. Thus, if hemoglobin test data is available, the hematocrit level is generally already known before start of the centrifuge-based sedimentation test.

Figure 18B:
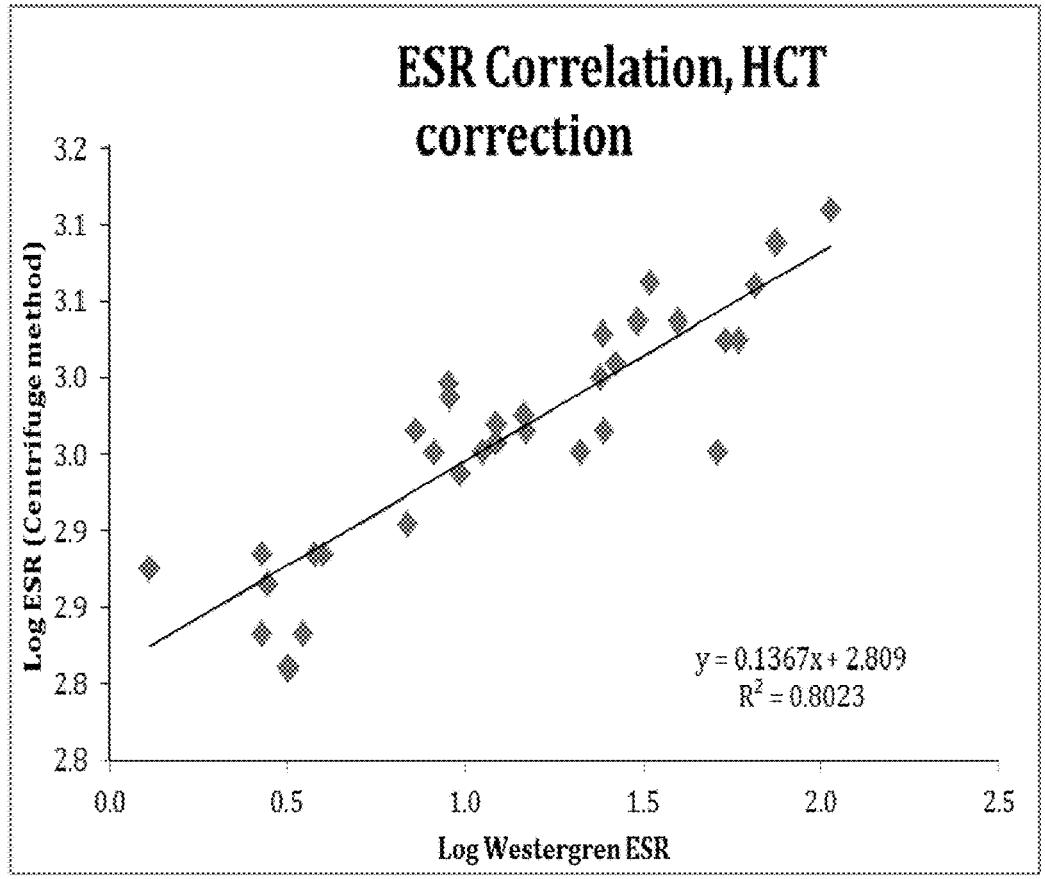
FIG. 18B shows an ESR graph of one embodiment herein with hematocrit correction.
Figure 18C:
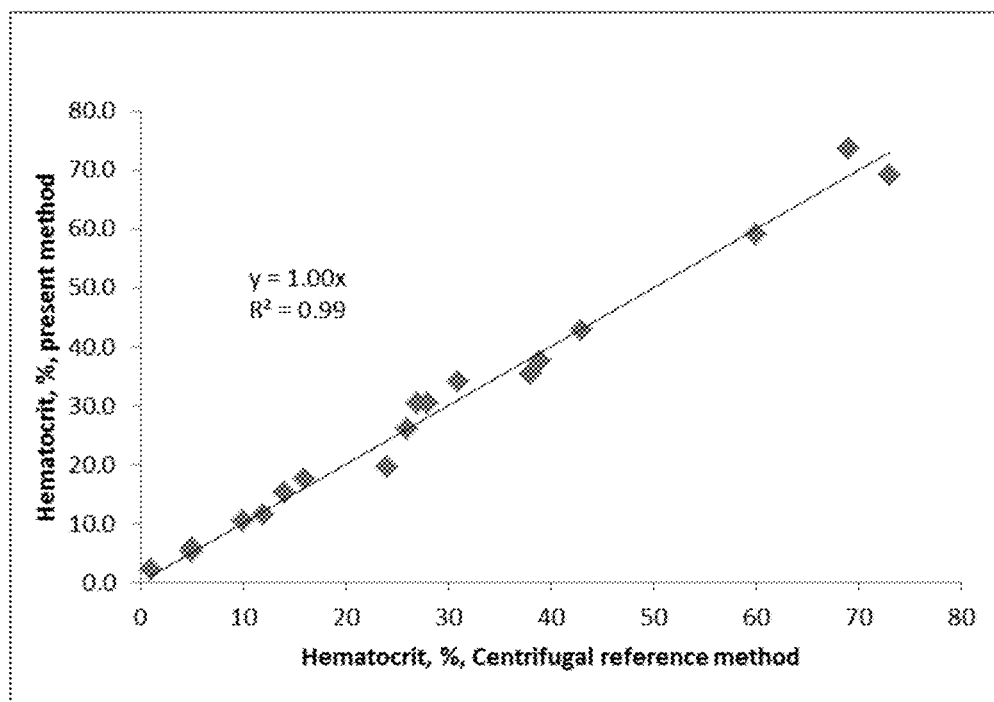
FIG. 18C shows a graph of hematocrit measurement based on hemoglobin concentration according to one embodiment herein.

Referring now to FIG. 18C, one embodiment of an assay protocol for hemoglobin-based hematocrit measurement will now be described. Blood was diluted 1:100 with water. The diluted sample was mixed (1:3) with modified Drabkin's reagent (Sigma D5941, containing sodium bicarbonate, potassium ferricyanide, and potassium cyanide supplemented with 0.015% Brij 35). After 10 minutes at 37 C, the absorbance of the reaction product (Cyan-met-hemoglobin) was measured at 540 nm. The assay was calibrated with bovine hemoglobin (Sigma 2500) which gave a linear dose-response over the range 0-20 g/dL.

Using an assay protocol for hemoglobin-based measurement, correlation of results with hematocrit measurement will now be discussed. Human blood samples were processed by recombining plasma and red cells (collected by centrifugation) to provide a wide range of hematocrit values. These samples were assayed as above and by a standard centrifugal capillary tube hematocrit assay and results correlated as shown below. As seen in FIG. 18C, the resulting correlation was accurate with slope=1, intercept=zero and correlation coefficient (R^2)=0.99.

Another technique for hematocrit measurement involves microscopic imaging. Hematocrit can also be measured in the devices using a cuvette with a fixed depth and a blood sample diluted to a known extent. Description of a system with such a cuvette can be found in U.S. patent application Ser. No. 13/244,947 fully incorporated herein by reference for all purposes. Hematocrit can be determined by microscopic measurement of the (1) the red cell count per field of view and (2) the average red cell volume. Favored methods are: (1) Dark field microscopy and (2) (1)+Fluorescence microscopy using fluorescently-labeled anti-human CD-35 (red cell surface antigen). Image analysis techniques are then applied.

Specifically, one method of measuring hematocrit may involve measuring optical density of the sample. See for example Lipowsky et al. "Hematocrit determination in small bore tubes from optical density measurements under white light illumination" Microvascular Research, Volume 20, Issue 1, July 1980, Pages 51-70, fully incorporated herein by reference for all purposes. Lipowsky discusses the relationship between the hematocrit of blood flowing in small bore glass tubes and its optical density (OD) under white light (tungsten) illumination has been examined for various tube luminal diameters. In at least some embodiments herein, all this data is available since a small-bore tube of blood is being illuminated.

In another embodiment, hematocrit level can be determined by testing a portion of the blood sample under microscopy or other magnified observation, such as but not limited to measuring the number and mean size of red blood cells in a defined observation area which may have a known size. In this manner, the hematocrit may be determined based on such visual characterization of the red blood cells.

In yet another example, hematocrit level can be measured based on a completed centrifugation of the blood sample which compacts the red blood cells. This compacted level can be used to determine hematocrit. In this example, only linear portions of the centrifuge based sedimentation test are used to determine a corrected ESR. By way of a non-limiting example, the first initial portion of interface position measurement which is linear, along with the final end portion which is also linear, are two portions of the sedimentation which may be used to calculate an ESR corrected for hematocrit. As seen in FIG. 9, this non-limiting example may use a linear portion 182 of the sedimentation curve corresponding to an initial period after centrifugation and another linear portion 184 of the sedimentation curve near the end when compaction is essentially complete curve is substantial flat. The non-linear portion of the sedimentation curve therebetween linear portions 182 and 184 are substantially not used to calculate the hematocrit correction factor.

The above is a non-exhaustive listing of hematocrit calculation techniques and other methods of measuring hematocrit levels are not excluded from use with the sedimentation measurement techniques described herein.

Graphs of Hematocrit Corrected ESR

FIG. 18B shows the logarithm of erythrocyte sedimentation rates extracted from sedimentation profiles corrected for the effect of hematocrit. As can be seen from the improvement in correlation coefficient the hematocrit correction (for example, see FIG. 18A) is capable of essentially eliminating the effects of hematocrit on ESR.

With hematocrit-adjusted clinical samples, good correlations with ESR within each hematocrit level, and, as expected, significant effects of hematocrit were also found. The centrifugation method can also be used to obtain accurate values for the hematocrit, and the impact of hematocrit can be corrected.

Figure 19:
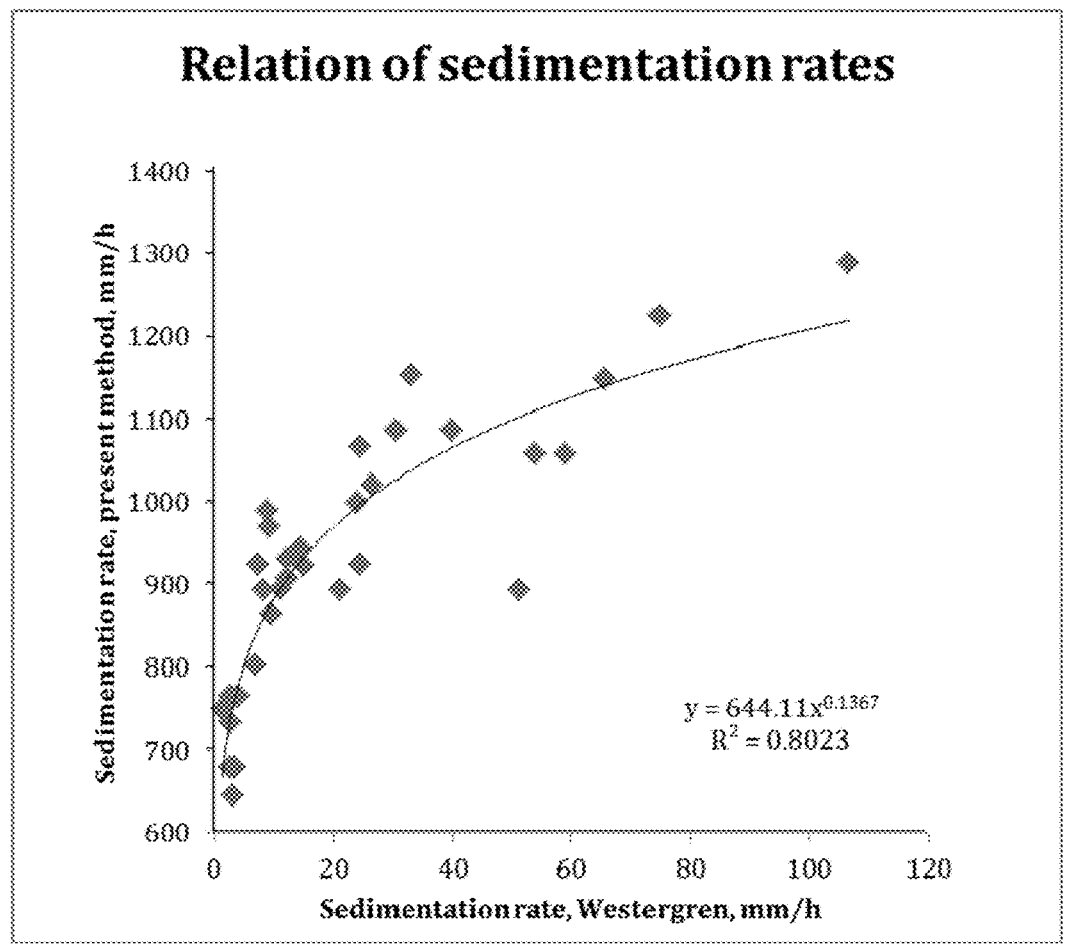
FIGS. 19 and 20 illustrate sedimentation rates for several samples (as specified in FIG. 15) plotted using non-LOG and LOG axis.

FIG. 19, shows a re-plot of the data of FIG. 18B in which the effects of hematocrit are clearly minimized as demonstrated by the good correlation of values of hematocrit-corrected ESR (present method) and ESR from traditional Westergren testing technique.

Figure 20:
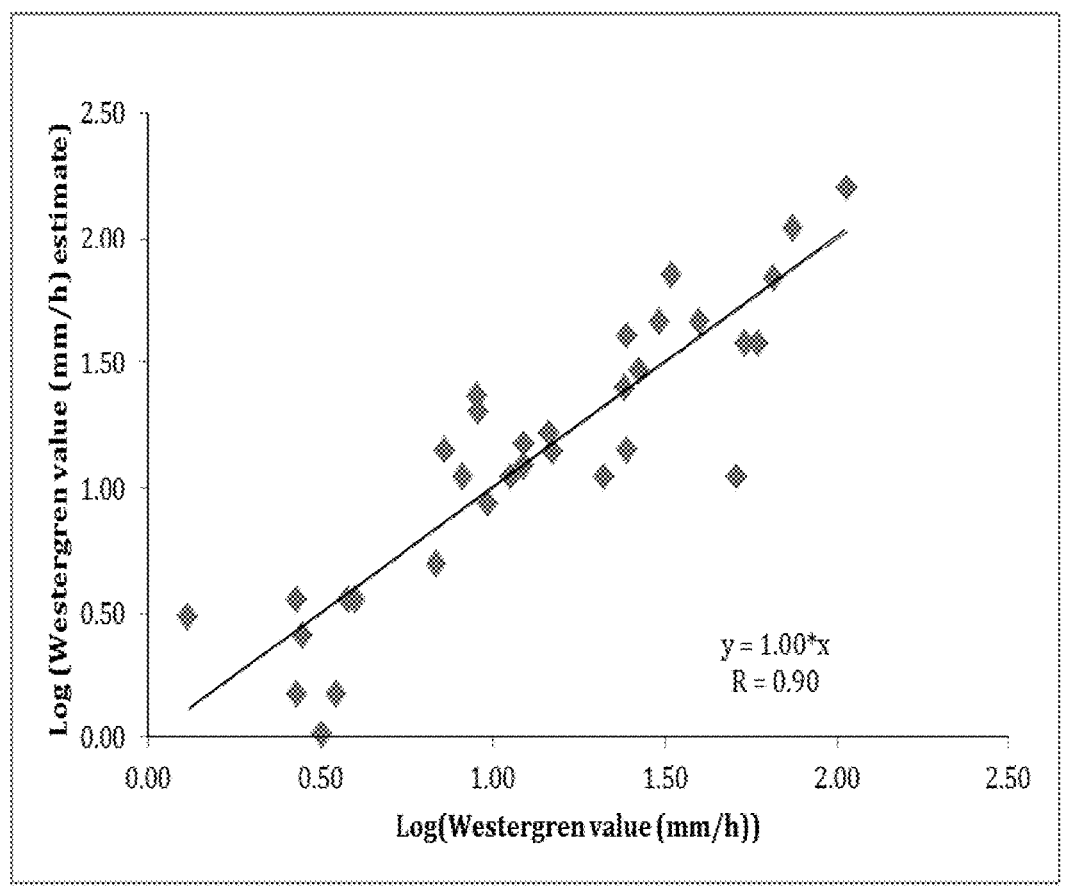

Referring now to FIG. 20, the relationship between the hematocrit-corrected ESR of the present method does not, however, have a linear relation to the Westergren ESR as seen in FIG. 19. To derive an estimate of the sedimentation rate that is linearly related to the Westergren ESR, the centrifuge-derived, hematocrit corrected data may be further corrected using the formula:

Estimated Westergren ESR=10^(((LOG(HCT corrected ESR)-LOG(644.11))/0.1367)), where the relationship and parameters used are derived from the analysis of FIG. 18B.

FIG. 20 shows that the hematocrit-corrected and linearly-transformed Log(ESR) values obtained by the present embodiment as a function of Westergren ESR (uncorrected for hematocrit). When the Log of the Estimated Westergren ESR from the centrifuge method was plotted against the log of the Westergren ESR as in FIG. 20, good correlation (R=0.90), slope (1.00) and intercept (0.00) values were obtained showing equivalence of the methods. Log values were plotted to show the fit across the wide range of ESR values found (almost 100-fold).

Experimental Methods

The data obtained for the various charts were obtained using the following techniques. These are provided as examples and are meant to be non-limiting.

Samples:

Fresh EDTA-anticoagulated blood samples were used. EDTA is used as this is the standard for the "Modified Westergren" method. Samples were kept at room temperature and re-suspended prior to measurement.

Hematocrit Adjustment:

Samples were spun down for hematocrit packing (e.g. 5000 Relative centrifugal force (RCF) for 20 minutes), and plasma is separated from the cells. Red blood cells were slurried with plasma from the same sample and more plasma added to give a desired hematocrit level.

Westergren ESR Measurements:

A 1 mL sample is required to perform the Westergren ESR measurement ('Sedigren' brand tubes used, following protocol enclosed therein). Red blood cell sedimentation was observed and measured by video recording.

Adjustment of RBC Zeta Potential (and ESR) with Fibrinogen:

For the examples shown in FIGS. 11-14, bovine fibrinogen was dissolved in blood. In one example, a range of 0-10 mg/mL produced a range of 5-100 mm/h ESR for a 40% hematocrit sample.

Measurement of Centrifuge Sedimentation Curve:

A 25 uL of whole blood sample was added to a centrifuge vessel. A swinging bucket centrifuge as described in co-pending U.S. patent application Ser. Nos. 13/355,458 and 13/244,947 were modified with a slot cut to allow light to pass through the bucket when spinning in a horizontal fashion (axis of rotation vertical). In this non-limiting example, the light source was 1W green LED, such as available from Thorlabs of Newton N.J., that is brightness adjusted (typically ~10%) so that light reaching the detector did not saturate it. A webcam or other imaging device such as available from Logitech was positioned at 10 mm above the plane of rotation as shown in FIG. 3. Integration time was 200 ms. Images were taken at 5 frames/second (fps) using a loss-less compression codec ("huffyuv") over known times up to three minutes.

Image Transformation:

images obtained visual observations of the centrifuge vessels during centrifugation were processed in the manner as described herein for FIGS. 6A to 7C.

Sedimentation Curve Extraction:

the position over time of the red blood cell/plasma and other interfaces in the images were then plotted in the manner as described herein for FIGS. 8A-9.

Curve Fitting with Hematocrit Correction Factor:

The sedimentation curve is then further processed by way of curve fitting using various techniques described herein for FIGS. 10A-10B and FIG. 16-20, with or without Hematocrit correction factor(s), to derive sedimentation rate information.

Measurement of Non-Red Blood Cell Blood Components

Although the present description is written primarily in the context of measuring erythrocyte sedimentation rate, it should be understood that the techniques herein can be adapted for use to measure sedimentation rates of other formed blood components that are not erythrocytes. Some embodiments may measure platelet sedimentation. Some embodiments may measure white blood cell sedimentation.

Figure 21:
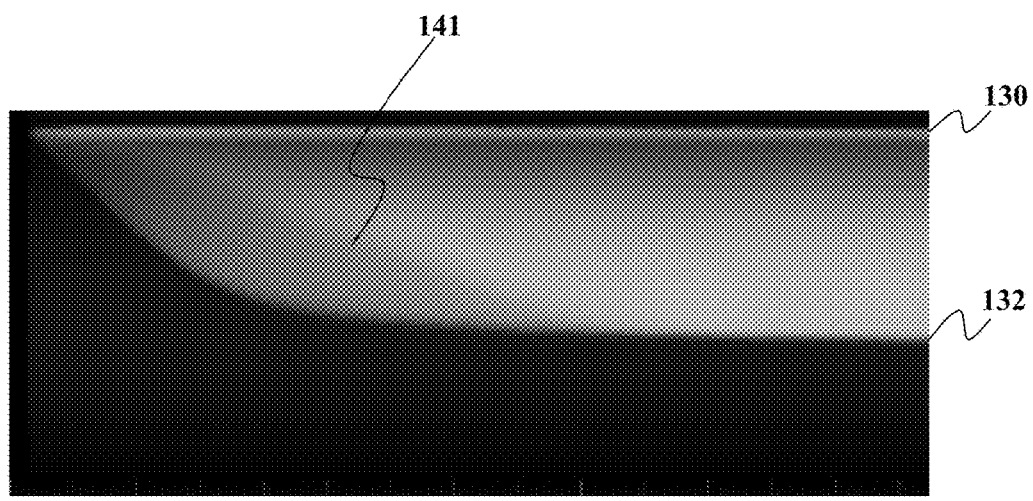
FIG. 21 shows a kymograph illustrating a white blood cell interface.

By way of nonlimiting example in FIG. 21, a kymograph obtained using the centrifuge based methods as described herein also shows that in addition to the air/plasma interface 130 and erythrocyte/plasma interface 132, there is also a "shadow" showing a white blood cell and plasma interface 141. Thus, both the red cell front and a second sedimentation front corresponding to white cells are observed in the sedimentation kymograph of FIG. 21.

Thus as seen in FIG. 21, some embodiments of the centrifugal method may be used to sequentially or simultaneously measure white blood cell sedimentation rate which may be useful in characterizing certain aspects of patient health. For example, white blood cells change their physical characteristics when they are activated and/or aggregated. Both phenomena are of great interest in evaluating white cell function. White cells sediment under centrifugal force, but they sediment at a rate more slowly than red blood cells. The rate of white blood cell sedimentation is a function of at least one of the following: white blood cell density, shape, and aggregation state. Measuring sedimentation rate can lead to detection of one or more these changes which may then be used characterize certain aspects of patient health.

By way of nonlimiting example, it should be understood that the use of change in refractive index or possibly light scattering can be used as a measure of the blood component interface position, rather than change in absorbance. Optionally, some embodiments may use both. FIG. 21 shows data indicating that the white blood cell interface is detectable due to refractive index or light scattering change rather than absorbance change. In one embodiment, RBC interface position is based on absorbance change due to the hemoglobin absorbing heavily in the green portion of the wavelength spectrum. RBC interface could perhaps be similarly monitored if light of the right wavelength were used (very long wavelength). Thus, using light scattering or change in refractive index can also be used alone or in combination with absorbance as an alternative way of measuring interface position or for detecting some interface(s) such as for white blood cells or platelets that are not readily visible by absorbance detection alone.

Assay Processing in an Integrated, Automated System

Figure 22:
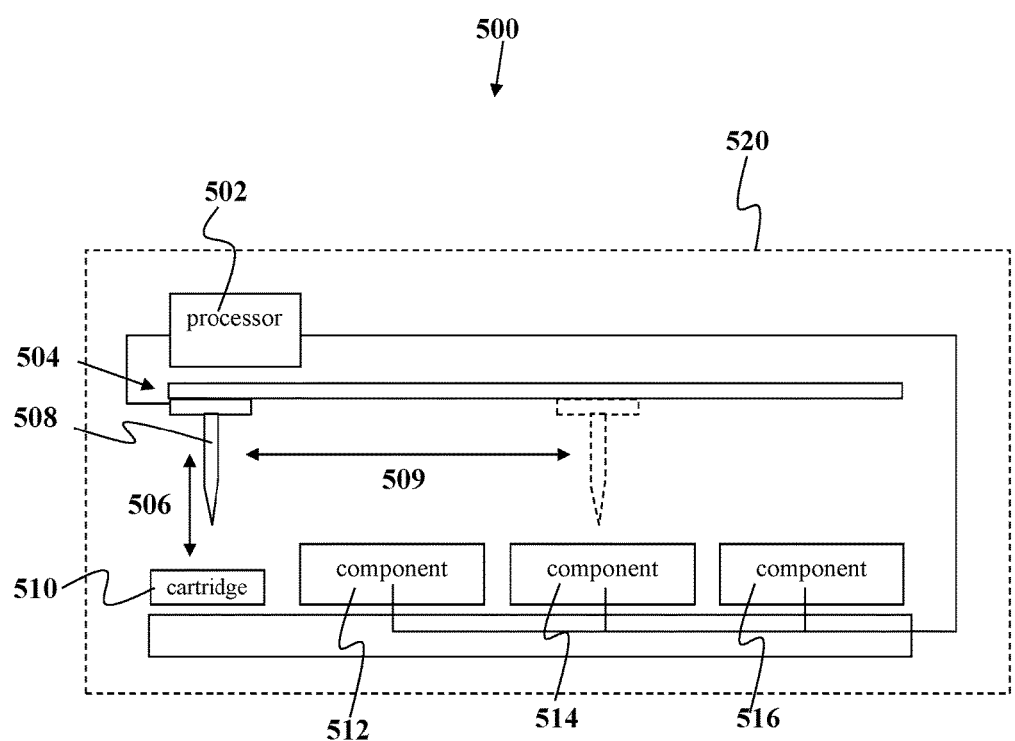
FIG. 22 shows a schematic of one embodiment of an integrated system having sample handling, pre-processing, and analysis components.

Referring now to FIG. 22, it should be understood that the processes described herein may be performed using automated techniques. The automated processing may be used in an integrated, automated system. In some embodiments, this may be in a single instrument having a plurality of functional components therein and surrounded by a common housing. The processing techniques and methods for sedimentation measure can be pre-set. Optionally, that may be based on protocols or procedures that may be dynamically changed as desired in the manner described in U.S. patent application Ser. Nos. 13/355,458 and 13/244,947, both fully incorporated herein by reference for all purposes.

In one non-limiting example as shown in FIG. 22, an integrated instrument 500 may be provided with a programmable processor 502 which can be used to control a plurality of components of the instrument. For example, in one embodiment, the processor 502 may control a single or multiple pipette system 504 that is movable X-Y and Z directions as indicated by arrows 506 and 509. The same or different processor may also control other components 512, 514, or 516 in the instrument. In one embodiment, tone of the components 512, 514, or 516 comprises a centrifuge.

As seen in FIG. 22, control by the processor 502 may allow the pipette system 504 to acquire blood sample from cartridge 510 and move the sample to one of the components 512, 514, or 516. Such movement may involve dispensing the sample into a removable vessel in the cartridge 510 and then transporting the removable vessel to one of the components 512, 514, or 516. Optionally, blood sample is dispensed directly into a container already mounted on one of the components 512, 514, or 516. In one non-limiting example, one of these components 512, 514, or 516 may be a centrifuge with an imaging configuration as shown in FIG. 3. Other components 512, 514, or 516 perform other analysis, assay, or detection functions.

All of the foregoing may be integrated within a single housing 520 and configured for bench top or small footprint floor mounting. In one example, a small footprint floor mounted system may occupy a floor area of about 4 $m^2$ or less. In one example, a small footprint floor mounted system may occupy a floor area of about 3 $m^2$ or less. In one example, a small footprint floor mounted system may occupy a floor area of about 2 $m^2$ or less. In one example, a small footprint floor mounted system may occupy a floor area of about 1 $m^2$ or less. In some embodiments, the instrument footprint may be less than or equal to about 4 $m^2$, 3 $m^2$, 2.5 $m^2$, 2 $m^2$, 1.5 $m^2$, 1 $m^2$, 0.75 $m^2$, 0.5 $m^2$, 0.3 $m^2$, 0.2 $m^2$, 0.1 $m^2$, 0.08 $m^2$, 0.05 $m^2$, 0.03 $m^2$, 100 $cm^2$, 80 $cm^2$, 70 $cm^2$, 60 $cm^2$, 50 $cm^2$, 40 $cm^2$, 30 $cm^2$, 20 $cm^2$, 15 $cm^2$, or 10 $cm^2$. Some suitable systems in a point-of-service setting are described in U.S. patent application Ser. Nos. 13/355,458 and 13/244,947, both fully incorporated herein by reference for all purposes. The present embodiments may be configured for use with any of the modules or systems described in those patent applications.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, with any of the above embodiments, it should be understood that other techniques for plasma separation may also be used with or in place of centrifugation. For example, one embodiment may centrifuge the sample for an initial period, and then the sample may be located into a filter that then removes the formed blood components to complete separation. Although the present embodiments are described in the context of centrifugation, other accelerated separation techniques may also be adapted for use with sedimentation rate measurement methods described herein. Some embodiments may optionally combine the hematocrit correction techniques described herein with measurement techniques as described in U.S. Pat. No. 6,204,066 fully incorporated herein by reference for all purposes. Some embodiments herein may pre-process the blood sample to pre-set the hematocrit value in the blood sample to a pre-determined value so that the variable due to hematocrit is removed. Some embodiments may also use traditional techniques for adjusting for hematocrit levels. It should also be understood that although the present embodiments are described in the context of blood samples, the techniques herein may also be configured to be applied to other samples (biological or otherwise).

Optionally, at least one embodiment may use a variable speed centrifuge. With feedback, such as but not limited to imaging of the position of interface(s) in the sample, the speed of the centrifuge could be varied to keep the compaction curve linear with time (until fully compacted), and the ESR data extracted from the speed profile of the centrifuge rather than the sedimentation rate curve. In such a system, one or more processors can be used to feedback control the centrifuge to have a linear compaction curve while speed profile of the centrifuge is also recorded. Depending on which interface is being tracked, the sedimentation rate data is calculated based centrifuge speed. In one non-limiting example, a higher centrifuge speed is used to keep a linear curve as the compaction nears completion.

Furthermore, those of skill in the art will recognize that any of the embodiments of the present invention can be applied to collection of sample fluid from humans, animals, or other subjects. Optionally, the volume of blood used for sedimentation testing may be 1 mL or less, 500 μL or less, 300 μL or less, 250 μL or less, 200 μL or less, 170 μL or less, 150 μL or less, 125 μL or less, 100 μL or less, 75 μL or less, 50 μL or less, 25 μL or less, 20 μL or less, 15 μL or less, 10 μL or less, 5 μL or less, 3 μL or less, 1 μL or less, 500 nL or less, 250 nL or less, 100 nL or less, 50 nL or less, 20 nL or less, 10 nL or less, 5 nL or less, or 1 nL or less.

Additionally, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a size range of about 1 nm to about 200 nm should be interpreted to include not only the explicitly recited limits of about 1 nm and about 200 nm, but also to include individual sizes such as 2 nm, 3 nm, 4 nm, and sub-ranges such as 10 nm to 50 nm, 20 nm to 100 nm, etc . . . .

The publications discussed or cited herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. All publications mentioned herein are incorporated herein by reference to disclose and describe the structures and/or methods in connection with which the publications are cited. The following applications are fully incorporated herein by reference for all purposes: U.S. patent application Ser. Nos. 13/355,458 and 13/244,947.

Various aspects of at least some embodiments described herein are enumerated in the following paragraphs:

Aspect 1. A method comprising: using an accelerated blood component separation technique on a blood sample for a period of time to separate formed blood components from plasma; establishing a time-related compaction curve for at least one formed blood component in said blood sample after accelerated blood component separation has begun, said compaction curve having an initial approximately linear portion; determining sedimentation rate of the formed blood component based on at least the following: the compaction curve and a hematocrit correction factor.

Aspect 2. A method comprising: centrifuging a blood sample in a vessel for a period of time; establishing a time-related compaction curve for at least one formed blood component in said blood sample after centrifuging has begun, said compaction curve having an initial approximately linear portion; correcting for hematocrit effect on sedimentation rate of the formed blood component by using a hematocrit correction factor on the approximately linear portion of said compaction curve.

Aspect 3. A method comprising: centrifuging a blood sample in a vessel for a period of time; establishing a time-related compaction curve for at least one formed blood component in said blood sample after centrifuging has begun; correcting for impact of hematocrit on sedimentation rate of the formed blood component using a hematocrit correction factor based on the formula:

$$U_{corr} = \frac{U_{uncorr}}{\left(1 - \frac{\varphi}{\varphi_{max}}\right)^{\gamma}},$$

where $U_{uncorr}$ and $U_{corr}$ are the uncorrected (raw) and corrected sedimentation rates, $\varphi$ is the volume fraction of cells (hematocrit), and $\varphi_{max}$ and $\gamma$ are empirical parameters obtained by curve fitting Aspect 4. The method of any one of the foregoing aspects, wherein curve fitting for the hematocrit correction factor comprises calibrating sedimentation rates from centrifuge based technique with sedimentation rates from a reference technique.

Aspect 5. The method of any one of the foregoing aspects, wherein the reference technique is the Westergren technique.

Aspect 6. The method of any one of the foregoing aspects, wherein fibrinogen levels as high as 15 mg/ml does not impact sedimentation rate measurement.

Aspect 7. The method of any one of the foregoing aspects, wherein said blood sample is about 100 uL or less.

Aspect 8. The method of any one of the foregoing aspects, wherein said blood sample is about 50 uL or less.

Aspect 9. The method of any one of the foregoing aspects, wherein said blood sample is about 25 uL or less.

Aspect 10. The method of any one of the foregoing aspects, wherein centrifugation occurs at a first speed for a first period of time and then at a second, faster speed for a second period of time.

Aspect 11. The method of any one of the foregoing aspects, wherein centrifugation uses a centrifuge configured to allow the blood sample to be visually observed during centrifugation to establish interface positions of one or more formed blood components in the blood sample.

Aspect 12. The method of any one of the foregoing aspects, wherein centrifugation uses a centrifuge having a window thereon to enable visual observation of the blood sample to establish erythrocyte/plasma interface positions over time.

Aspect 13. The method of any one of the foregoing aspects, wherein centrifugation uses a centrifuge, a light source, and an image capture device to enable visual observation of the blood sample to establish formed blood component/plasma interface positions over time.

Aspect 14. The method of any one of the foregoing aspects, wherein compaction curve data is collected by capturing a plurality of images of interface positions of one or more formed blood components in the centrifuge vessel over the time period.

Aspect 15. The method of aspect 14, wherein pixel positions in the plurality of images are used to accurately determine interface position.

Aspect 16. The method of aspect 14, wherein capturing of images begins once the centrifuge has reached a minimum operating speed.

Aspect 17. The method of aspect 14, wherein capturing of images begins when the centrifuge has begins rotation.

Aspect 18. The method of any one of the foregoing aspects, wherein compaction curve data is collected while the sample is being centrifuged.

Aspect 19. The method of any one of the foregoing aspects, wherein centrifugation is used to obtain accurate values for the hematocrit and to correct for hematocrit impact on sedimentation rate measurement.

Aspect 20. The method of any one of the foregoing aspects, wherein correcting for hematocrit comprises calculating a mathematical function for a plurality of formed blood component interface positions occurring in said curve, said function being operative to correct for sedimentation rate variations due to hematocrit.

Aspect 21. The method of any one of the foregoing aspects, wherein hematocrit correction factor is determined without using data from a non-linear portion of the compaction curve.

Aspect 22. The method of any one of the foregoing aspects, wherein hematocrit level in the sample is derived from a technique separate from centrifugation.

Aspect 23. The method of any one of the foregoing aspects, wherein $\varphi_{max}$ and $\gamma$ are for fit optimization and do not relate directly to physical parameters.

Aspect 24. The method of any one of the foregoing aspects, further comprising image transformation for conversion of a curved interface to a flat interface.

Aspect 25. The method of any one of the foregoing aspects, wherein hematocrit correction is capable of essentially eliminating the effects of hematocrit on formed blood component sedimentation rate.

Aspect 26. The method of any one of the foregoing aspects, wherein image transformation parameters are selected, video of formed blood component interface position is put through image transformation, and then a region of interest is chosen that covers both the whole range of positions for both air/plasma interface and erythrocyte interface.

Aspect 27. The method of any one of the foregoing aspects, wherein for each timepoint in the video, pixel intensity values for each row across the sample vessel within the region of interest are averaged to produce a single column representing the intensity radially down the sample vessel.

Aspect 28. The method of any one of the foregoing aspects, wherein columns for each timepoint are then assembled into a kymograph.

Aspect 29. The method of aspect 28 wherein positions of the two local maxima of the image, one representing the air/plasma interface and other the plasma/erythrocyte interface are determined.

Aspect 30. The method of aspect 28 comprising converting pixel positions into volume occupied by the whole sample and volume occupied by red blood cells, wherein the y-position of the top and bottom of the centrifuge vessel are used as reference locations together with knowledge of the shape of the centrifuge vessel.

Aspect 31. The method of any one of the foregoing aspects comprising converting plasma/erythrocyte interface position to the volume fraction occupied by red blood cells and plotted against time as a centrifuge sedimentation curve.

Aspect 32. The method of any one of the foregoing aspects, wherein a linear region of a sedimentation profile is used to extract a sedimentation rate.

Aspect 33. The method of any one of the foregoing aspects, further comprising deriving an estimate of the sedimentation rate linearly related to the Westergren ESR, the centrifuge-derived, hematocrit corrected data further corrected using the formula: Estimated Westergren ESR=10^(((LOG(HCT corrected ESR)-LOG(a))/b)).

Aspect 34. The method of any one of the foregoing aspects, further comprising hematocrit-correcting and linearly-transforming Log(ESR) values to establish a linear graph of sedimentation rate.

Aspect 35. The method of any one of the foregoing aspects wherein the blood sample is whole blood.

Aspect 36. The method of any one of the foregoing aspects wherein the blood sample is an anti-coagulated sample.

Aspect 37. The method of any one of the foregoing aspects wherein the formed blood component is white blood cells.

Aspect 38. The method of any one of the foregoing aspects wherein the formed blood component is platelets.

Aspect 39. The method of any one of the foregoing aspects, further comprising determining white cell sedimentation rate after centrifugation has begun, wherein measuring white cell sedimentation rate characterizes at least one of the following regarding the white blood cells: cell density, shape, and aggregation state.

Aspect 40. A method comprising: collecting a plurality of images of formed blood component and plasma interface positions over time from an accelerated blood sample compaction process; performing image transformation on said plurality of images to transform images with curved interfaces into corrected images with straight line interfaces; establishing a time-related compaction curve based on interface positions in said corrected images, for at least one formed blood component in said blood sample.

Aspect 41. A method comprising: centrifuging a blood sample in a vessel for a period of time; collecting a plurality of images of formed blood component and plasma interface positions over time; performing image transformation on said images to transform images with curved interfaces into corrected images with straight line interfaces; establishing a time-related compaction curve based on interface positions in said corrected images, for at least one formed blood component in said blood sample after centrifuging has begun.

Aspect 42. A method comprising: using a programmable processor-controlled system to transfer at least a portion of a blood sample from a blood sample location into a centrifugation vessel; using a sample handling system under programmable processor control to transfer said vessel from a first addressable position to a centrifuge with a second addressable position; centrifuging the blood sample in the vessel for a period of time; collecting a plurality of images of formed blood component and plasma interface positions over time;

establishing a time-related compaction curve based on interface positions in said corrected images, for at least one formed blood component in said blood sample after centrifuging has begun.

Aspect 43. The method of any one of the foregoing aspects, wherein the centrifuge has a rotor with a diameter of about 15 cm or less.

Aspect 44. The method of any one of the foregoing aspects, wherein the centrifuge has a rotor with a diameter of about 10 cm or less.

Aspect 45. The method of any one of the foregoing aspects, wherein the centrifuge has a rotor when in motion circumscribes an area with a longest dimension of about 15 cm or less.

Aspect 46. The method of any one of the foregoing aspects, wherein the centrifuge has a rotor when in motion circumscribes an area with a longest dimension of about 10 cm or less.

Aspect 47. A method comprising: centrifuging a blood sample in a vessel for a period of time; varying centrifuging speed to establishing a linear compaction curve of at least one formed blood component over the period of time until compacting has completed; monitoring centrifuging speed profile for at least a portion of the time period; and determining blood component sedimentation rate based on the centrifuging speed profile.

Aspect 48. A method comprising: centrifuging a blood sample in a vessel for a period of time; collecting at least a first single image of formed blood component and plasma interface positions at an initial time; collecting at least a second single image of formed blood component and plasma interface positions at a second time while rate of sedimentation is still linear; calculating sedimentation rate for at least one formed blood component in said blood sample based on linear sedimentation rate calculated and a hematocrit correction factor.

Aspect 49. A device for use with a sample, the device comprising:
a centrifuge having a centrifuge vessel holder configured to allow for detection of blood component interface position in the vessel holder during centrifugation.

Aspect 50. The device of aspect 49, wherein the centrifuge has window to allow for visual observation of the centrifuge vessel holder during centrifugation.

Aspect 51. The device of aspect 49, wherein the centrifuge an illumination source to allow for detection of blood component interface position in the sample.

Aspect 52. A system comprising: a centrifuge having a centrifuge vessel holder configured to allow for detection of blood component interface position in the vessel holder in the vessel holder during centrifugation; a sample handling system for transporting a blood sample from a first location to a location on the centrifuge; and a processor programmed to record interface position during a least a portion of centrifugation.

While the above is a complete description of the various embodiments of the present invention, it is possible to use various alternatives, modifications and equivalents. Therefore, the scope of the present invention should be determined not with reference to the above description but should, instead, be determined with reference to the appended claims, along with their full scope of equivalents. Any feature, whether preferred or not, may be combined with any other feature, whether preferred or not. The appended claims are not to be interpreted as including means-plus-function limitations, unless such a limitation is explicitly recited in a given claim using the phrase "means for." It should be understood that as used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise. Finally, as used in the description herein and throughout the claims that follow, the meanings of "and" and "or" include both the conjunctive and disjunctive and may be used interchangeably unless the context expressly dictates otherwise. Thus, in contexts where the terms "and" or "or" are used, usage of such conjunctions do not exclude an "and/or" meaning unless the context expressly dictates otherwise.

What is claimed is:

1. A method comprising:
using an accelerated blood component separation technique using a first compaction force on a blood sample for a first period of time, wherein the accelerated blood component separation technique occurs at a first module of a benchtop, point-of-service system and wherein the blood sample is contained in a non-capillary vessel;
moving the vessel from the first module to an imaging module all within a housing of the point-of-service system;
imaging the vessel to determine a position of formed component and plasma boundary in the vessel;
moving the vessel from the imaging module back to the first module;
using the accelerated blood component separation technique on the blood sample for a second period of time at a second compaction force greater than the first compaction force associated with the first period of time;
moving the vessel from the first module to an imaging module after the second period of time;
imaging the vessel to determine a second position of formed component and plasma boundary in the vessel after the second period of time;
determining a time-related compaction curve for at least one formed blood component in said blood sample after accelerated blood component separation based on the first position and the second position, said compaction curve having an initial approximately linear portion; and
determining sedimentation rate of the formed blood component in said accelerated blood component separation technique, based on at least the linear portion of the compaction curve and a hematocrit correction factor based on a hematocrit of the sample.

2. The method of claim 1 wherein the accelerated blood component separation technique comprises centrifuging the blood sample.

3. The method of claim 2, wherein formed component and plasma boundary comprise an erythrocyte/plasma interface boundary.

4. The method of claim 2, further comprising image transformation for conversion of a curved liquid interface to a flat interface.

5. The method of claim 2, further comprising using a processor programmed to record interface position during a least a portion of centrifugation.

6. The method of claim 2 wherein the non-capillary vessel comprises a centrifuge vessel.

7. The method of claim 1 comprises correcting for hematocrit effect on sedimentation rate by using the hematocrit correction factor based on the formula:

$$U_{corr} = \frac{U_{uncorr}}{\left(1 - \frac{\varphi}{\varphi_{max}}\right)^{\gamma}},$$

where $U_{uncorr}$ and $U_{corr}$ are the uncorrected (raw) and corrected sedimentation rates, $\varphi$ is the volume fraction of cells (hematocrit), and $\varphi_{max}$ and $\gamma$ are empirical parameters obtained by curve fitting.

8. The method of claim 7 wherein curve fitting for the hematocrit correction factor comprises calibrating sedimentation rates from centrifuge based technique with sedimentation rates from a reference technique.

9. The method of claim 8, wherein the reference technique is the Westergren technique.

10. The method of claim 1, wherein said blood sample is about 100 uL or less.

11. The method of claim 1, wherein said blood sample is about 50 uL or less.

12. The method of claim 1, wherein correcting for hematocrit comprises calculating a mathematical function for a plurality of formed blood component interface positions occurring in said curve, said function being operative to correct for sedimentation rate variations due to hematocrit.

13. The method of claim 1 wherein the blood sample being processed has a volume in the vessel of about 20-25 uL.

\* \* \* \* \*